US011883305B2

(12) United States Patent
Herr et al.

(10) Patent No.: US 11,883,305 B2
(45) Date of Patent: Jan. 30, 2024

(54) COMPUTER-CONTROLLED ANKLE-FOOT PROSTHESIS WITH SERIES J-SPRING ACTUATION

(71) Applicant: Massachusetts Institute of Technology, Cambridge, MA (US)

(72) Inventors: Hugh M. Herr, Concord, NH (US); Matthew Lawrence Handford, Cambridge, MA (US); Christopher Charles Williams, Pittsburgh, PA (US); Matthew Eli Carney, Medford, MA (US); Daniel Visan Levine, Decatur, GA (US)

(73) Assignee: Massachusetts Institute of Technology, Cambridge, MA (US)

( * ) Notice: Subject to any disclaimer, the term of this patent is extended or adjusted under 35 U.S.C. 154(b) by 243 days.

(21) Appl. No.: 17/455,884

(22) Filed: Nov. 19, 2021

(65) Prior Publication Data
US 2022/0160522 A1 May 26, 2022

Related U.S. Application Data

(60) Provisional application No. 63/117,395, filed on Nov. 23, 2020.

(51) Int. Cl.
*A61F 2/66* (2006.01)
*A61F 2/68* (2006.01)
*A61F 2/50* (2006.01)

(52) U.S. Cl.
CPC .............. *A61F 2/6607* (2013.01); *A61F 2/68* (2013.01); *A61F 2002/5003* (2013.01);
(Continued)

(58) Field of Classification Search
CPC ............ A61F 2/6607; A61F 2002/6664; A61F 2002/6614; A61F 2/68; A61F 2002/5003; A61F 2002/507
See application file for complete search history.

(56) References Cited

U.S. PATENT DOCUMENTS 5,252,102 A * 10/1993 Singer .................. G05B 19/408
623/24
8,317,876 B2 * 11/2012 Mosler ...................... A61F 2/66
623/47
(Continued)

FOREIGN PATENT DOCUMENTS

WO 2008103917 A1 8/2008

OTHER PUBLICATIONS

International Search Report and the Written Opinion of the International Searching Authority, dated Feb. 7, 2022, entitled "Computer-Controlled Ankle-Foot Prosthesis with Series J-Spring Actuation," for International Application No. PCT/US2021/072530.
(Continued)

*Primary Examiner* — Bruce E Snow
(74) *Attorney, Agent, or Firm* — Hamilton, Brook, Smith & Reynolds, P.C.

(57) ABSTRACT

An ankle-foot prosthesis comprises a foot structure having a foot keel leaf spring, a heel leaf spring, and an upper J leaf spring above the keel leaf spring. An ankle bearing block is mounted to the keel leaf spring and a shank shell is mounted to the ankle bearing block. A shank interface mounts to the shank shell. A processor controlled active element extends along an axis between the shank shell and the upper leaf-spring.

16 Claims, 21 Drawing Sheets

(52) U.S. Cl.
CPC . *A61F 2002/507* (2013.01); *A61F 2002/6664* (2013.01); *A61F 2002/6854* (2013.01)

(56) References Cited

U.S. PATENT DOCUMENTS

| | | | |
|---|---|---|---|
| 9,060,883 B2 | 6/2015 | Herr et al. | |
| 10,342,681 B2 | 7/2019 | Herr et al. | |
| 10,390,974 B2 | 8/2019 | Clausen et al. | |
| 10,543,109 B2* | 1/2020 | Holgate | B25J 19/0091 |
| 2010/0179668 A1* | 7/2010 | Herr | G01L 5/0028 |
| | | | 623/53 |
| 2014/0088729 A1 | 3/2014 | Herr et al. | |
| 2014/0243997 A1* | 8/2014 | Clausen | A61F 2/66 |
| | | | 623/55 |
| 2019/0321201 A1 | 10/2019 | Herr et al. | |
| 2022/0273466 A1* | 9/2022 | Nijman | A61F 2/6607 |

OTHER PUBLICATIONS

EmPower Ankle-Foot Product, Date unknown but prior to Nov. 19, 2020.
Empower Prosthetic Foot Product, Ottobock, 2020.
BiOM Bionic Prosthetic Device by Hugh Herr, Boston Business Journal, Dec. 30, 2014.

* cited by examiner

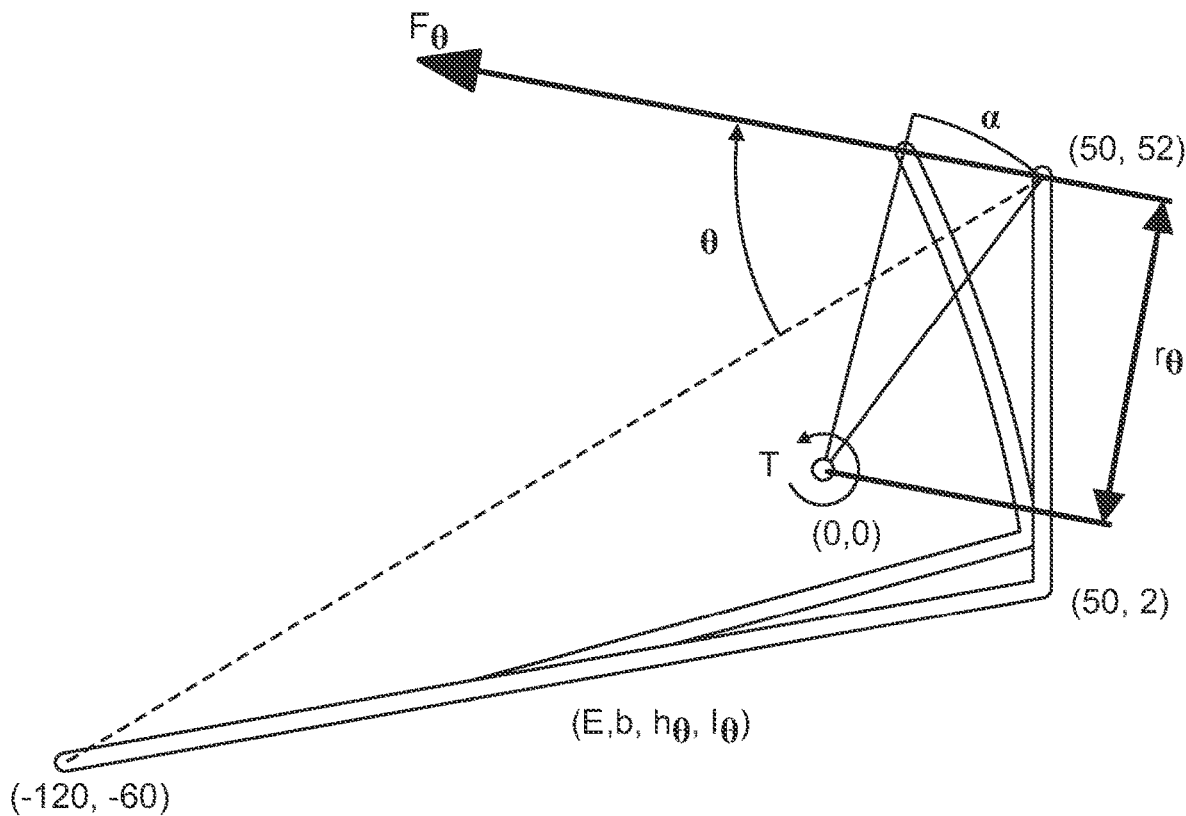

Constants, Variables, and Equations

| | | |
|---|---|---|
| Joint Torque | $T$ | $= 120$ Nm |
| Quasi-Stiffness | $K$ | $= 292$ Nm/rad |
| Modulus of Elasticity | $E$ | $= 220$ Gpa |
| Spring Width | $b$ | $= 35$ mm |
| Joint Angle | $\alpha$ | $= T/K$ |
| Active Element Axis Angle | $\theta$ | |
| Moment Arm | $r_\theta$ | $= f_r(\theta)$ |
| Force | $F_\theta$ | $= T/r_\theta$ |
| Thickness | $h_\theta$ | $= f_h(\theta)$ |
| Area Moment of Inertia | $I_\theta$ | $= bh_\theta^3/12$ |

FIG. 10C

COMPUTER-CONTROLLED ANKLE-FOOT PROSTHESIS WITH SERIES J-SPRING ACTUATION

RELATED APPLICATION

This application claims the benefit of U.S. Provisional Application No. 63/117,395, filed on Nov. 23, 2020. The entire teachings of the above application are incorporated herein by reference.

GOVERNMENT SUPPORT

This invention was made with Government support under Grant No. W81XWH-19-1-0151 awarded by the U.S. Army. The Government has certain rights in the invention.

BACKGROUND OF THE INVENTION

Ankle-foot prostheses are designed to restore the mobility of persons with lower-extremity amputation. To emulate the function of the biological ankle-foot complex, the ankle-foot prosthesis needs to be capable of providing impedance and torque control while on the ground, and position control while off the ground. For a typical walking gait, prostheses can accomplish these requirements through ankle impedance control during early stance, energy storage modulation during midstance, powered plantar flexion during late stance, and spring equilibrium control during the swing phase. If an ankle-foot prosthesis can perform these tasks without being too heavy, the user can maintain a comfortable and economical walking gait during everyday use. Most commercially-available ankle-foot prostheses approximate some of these capabilities through a passive composite spring structure. While passive prostheses work well on level ground at slow walking speeds, they are unable to adapt to changes in walking speed, ground slope, or stair ascent/descent in a manner that emulates biological function. Additionally, such passive designs do not provide any net positive work during the late stance period, increasing musculoskeletal stress and metabolic consumption during walking. Quasi-passive prostheses have been developed to allow the prosthesis to adapt to various tasks and walking conditions (e.g. Ottobock Meridium and Ossur Proprio Foot) through the computer-controlled modulation of ankle damping or swing phase ankle position. However, such commercial devices do not provide stiffness modulation during stance-phase controlled plantar flexion or controlled dorsiflexion, nor do such commercial devices provide net positive work during late stance powered plantar flexion. Active prostheses like the Ottobock EmPower address these issues using onboard computers and powerful motors, making walking more economical and comfortable. However, the EmPower has a much higher mass and build-height when compared to its passive and quasi-passive counterparts, making it challenging to use for lightweight users, or users with a limited stature.

SUMMARY OF THE INVENTION

Under microprocessor-control, the ankle-foot prosthesis presented herein will enable ankle impedance and ankle spring equilibrium modulation in an updating manner across gait phase, walking speed, and terrain. Additionally, the prosthesis will also provide powered plantar flexion with net mechanical work during the late stance period of walking. Given the novel architecture, all these capabilities are made possible with a reduced device mass, build height and acoustic noise level as compared to the commercially-available power ankle-foot prosthesis—the EmPower by Ottobock. These objectives are accomplished through the design of an ankle-foot device with a shank member connected to a foot keel spring via an ankle rotational joint comprising a bearing or a material flexor. A heel leaf spring is attached below the keel spring from the anterior aspect extending rearwardly to its posterior end. The posterior end of the heel spring touches the ground first at heel strike in a walking gait cycle, compressing towards the posterior aspect of the keel leaf spring to enable an increased level of shock absorption at foot strike.

Powering the ankle-foot device may be a series-elastic actuator optimized for the user to ensure a comfortable walking gait with low noise and reduced mass. The actuator comprises an upper leaf spring, specifically a J-spring (a passive-elastic, curved leaf-spring), spanning from the anterior aspect of the prosthetic keel spring to the posterior-proximal region of the device above the ankle rotational joint. In addition, the actuator comprises a computer-controlled active element connecting the posterior-proximal end of the J-spring to the prosthetic shank member via rotational bearing elements on either end of the active element.

Embodiments of an ankle-foot prosthesis comprise a foot structure. The foot structure comprises an anterior portion and a foot keel leaf-spring extending posteriorly from the anterior portion. An ankle-bearing block is mounted to and above the foot keel leaf-spring. A shank shell is mounted to and above the ankle-bearing block at an ankle joint. A prosthetic shank interface is mounted to the shank shell. An upper leaf-spring extends posteriorly from the anterior portion of the foot structure above the keel leaf-spring past the ankle-bearing block. A processor controlled active element extends along an active element axis between the shank shell and a posterior portion of the upper leaf-spring and is coupled to the shank shell at a shank shell rotational bearing and to the upper leaf-spring at an upper leaf-spring rotational bearing.

The foot structure may also include a heel leaf spring extending posteriorly from the anterior portion below the foot keel leaf spring. Or the foot keel leaf spring may itself serve the heal function.

The upper leaf-spring may be a J-spring that curves upwardly from the anterior portion to the posterior portion of the upper leaf-spring, the active element axis extending posteriorly from the shank shell rotational bearing to the upper leaf-spring rotational bearing.

The active element axis may extend, through a full operating range, at or above a toe line extending from the upper leaf-spring rotational bearing to an anterior end of the upper leaf-spring. At peak dorsiflexion, the active element axis may extend about parallel to an anterior length of the upper leaf-spring. Through a full operating range, the active element axis may be within about 45 degrees of being parallel to an anterior length of the upper leaf-spring.

In a first embodiment, the active element is a processing modulated damper with passive parallel return spring.

In a second embodiment, the active element is a processing modulated damper operatively coupled to a motor configured to enable processor modulation of the active element.

In a third embodiment, the active element is a motor-driven screw configured to enable processor modulation of the active element length. The screw may be a roller screw. It may be belt-driven or direct driven from the motor.

In a fourth embodiment, a clutch or variable damper is configured to lock the active element length.

The ankle-foot prosthesis may comprise a processor. It may further comprise sensors that sense operation of the ankle-foot prosthesis and provide input to the processor for control of the active element. It may further comprise at least one sensor from the group of sensors comprising inertia measurement units, joint encoders, motor encoders, force sensors and distance sensors.

BRIEF DESCRIPTION OF THE FIGURES

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 10A-C: A) J-spring diagram for various active element angles. B) The results of the simulation with θ ranging from −10° to 60° (−0.17 to 1.05 radians). C) Description of the simulation set up.

DETAILED DESCRIPTION OF THE INVENTION

Figure 1A:
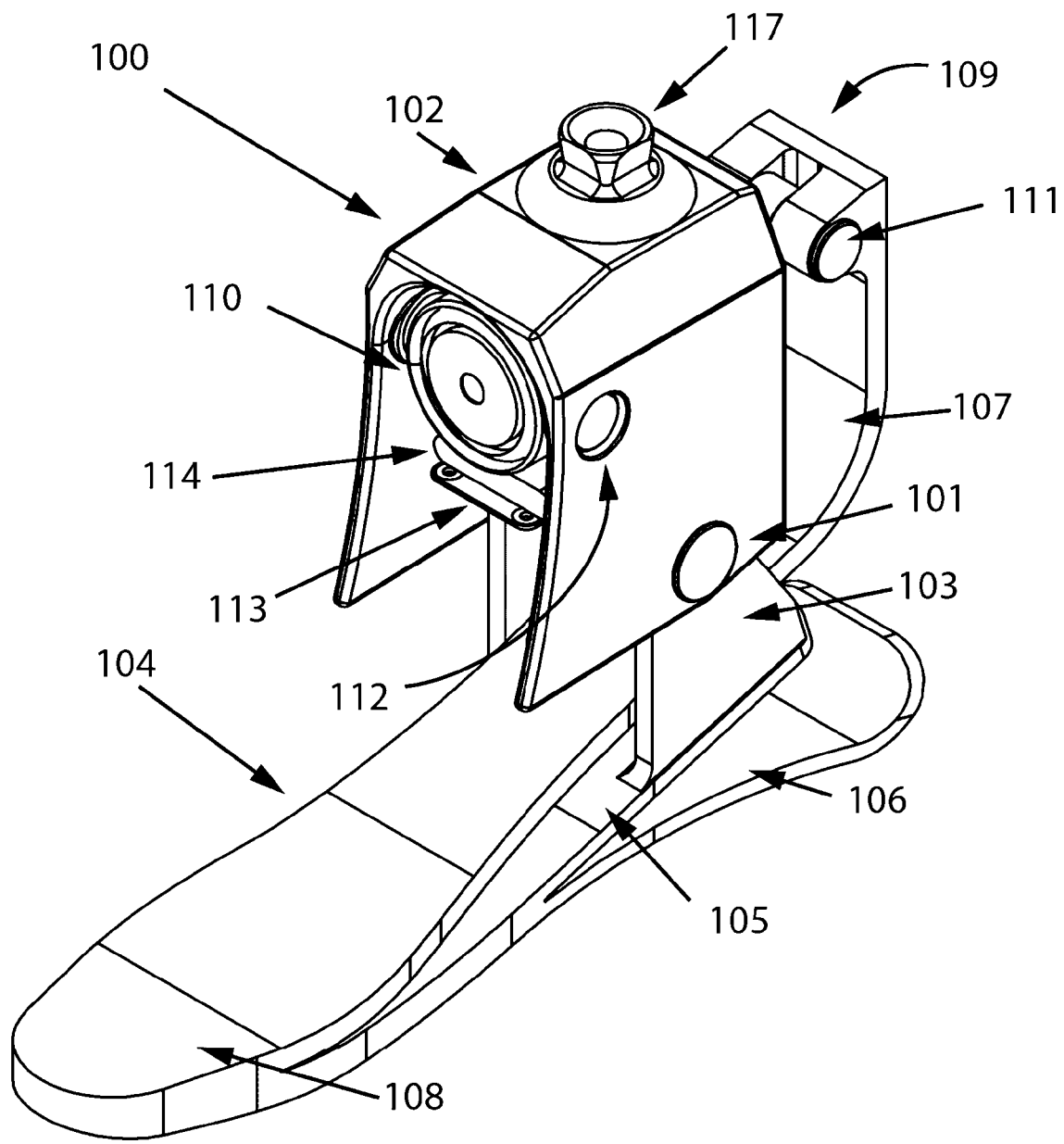
FIGS. 1a and b: Computer-controlled ankle-foot prostheses with series J-spring actuation, shown with drive active element.

A description of example embodiments follows.

In FIGS. 1, 2, 3, 4, and 8, lower case letters "a" and "b" are added to figure numbers to indicate earlier and later versions of primary embodiments. Identical reference numerals, without "a" and "b" designations, are used in the a and b figures as the common description applies to each figure and each element.

Figure 1B:
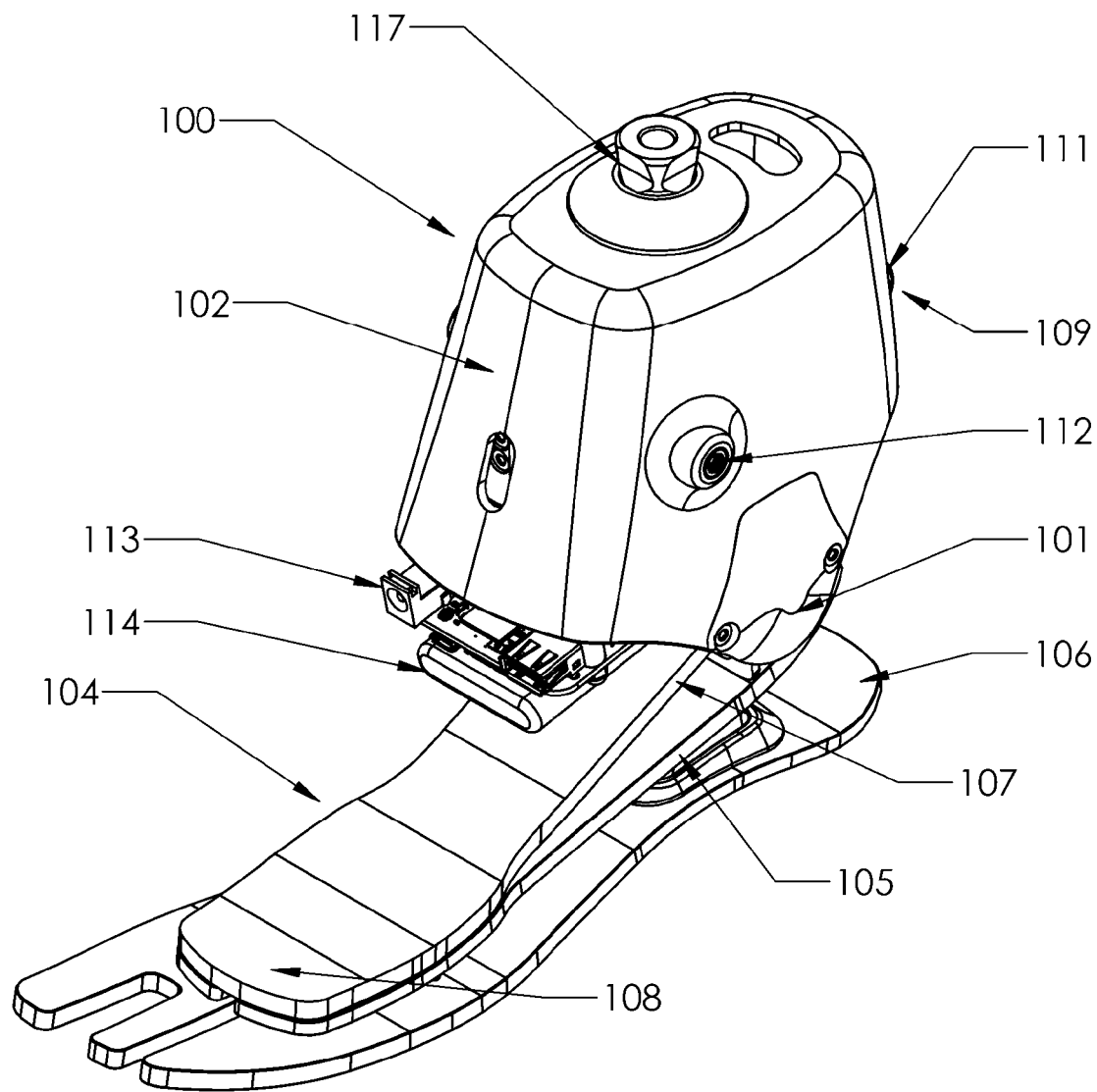
Figure 2A:
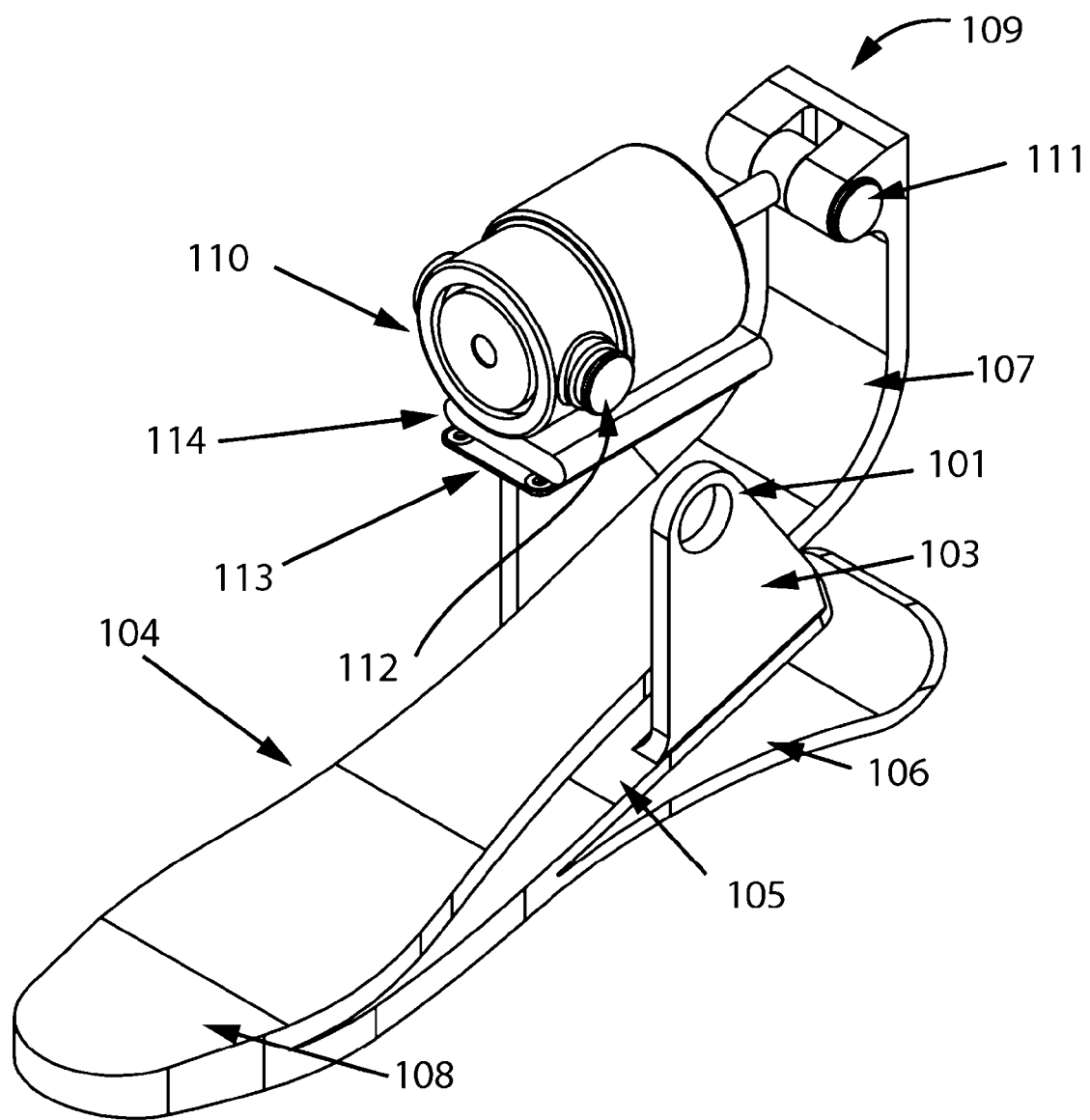
FIGS. 2a and b: Prostheses without the shank shell.
Figure 2B:
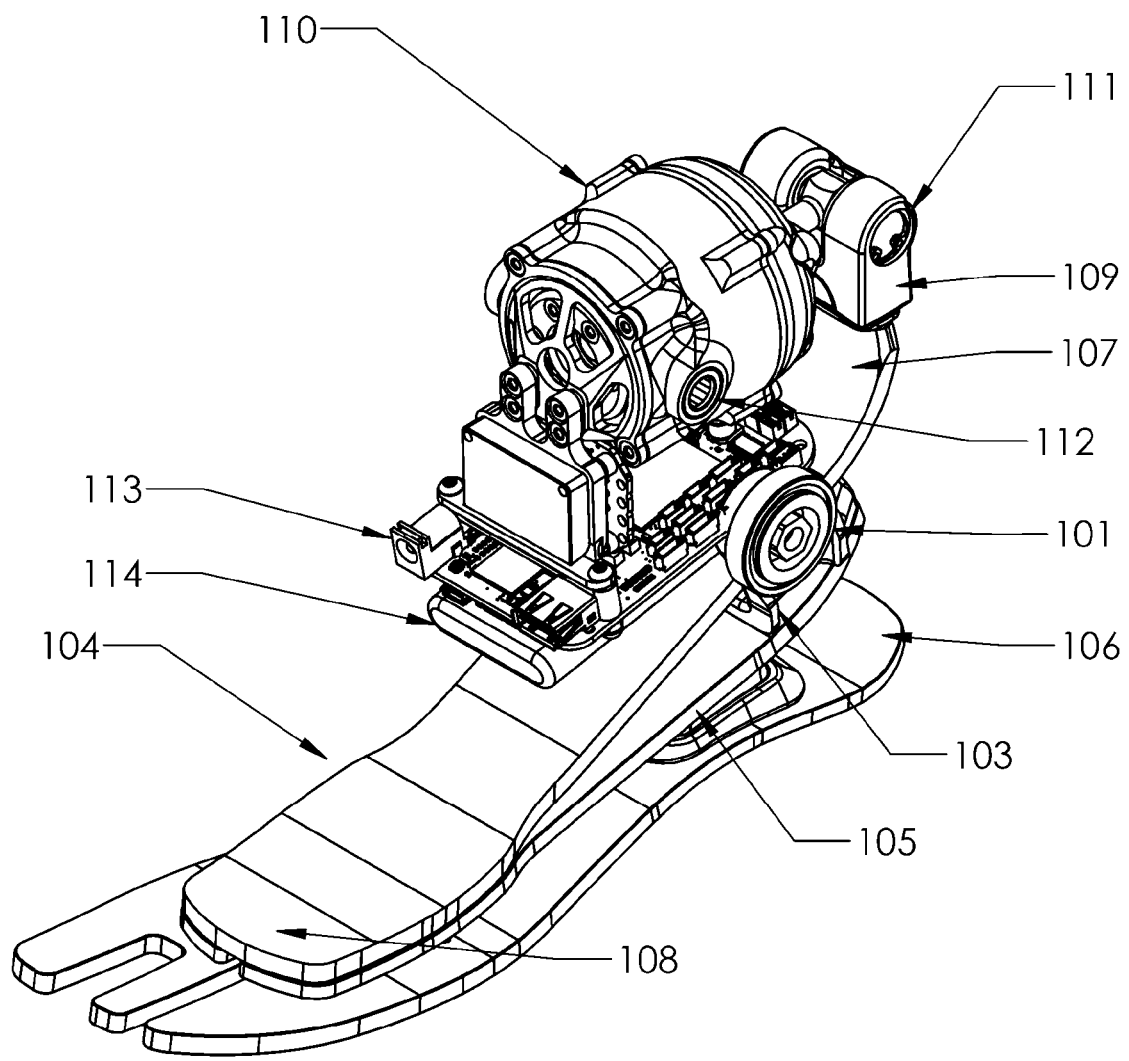

Shown in each of FIGS. 1a-4a and FIGS. 1b-4b is a computer-controlled prosthetic ankle-foot device 100 with an articulated ankle joint 101 connecting a shank shell component 102 and an ankle-bearing block 103. The ankle-bearing block 103 attaches to a carbon composite foot structure 104 comprising a foot keel spring 105 and heel spring 106. In FIG. 1b, a cushion is positioned between the keel spring 105 and heel spring 106. Such an elastomeric cushion insert can be used to adjust the stiffness of the combined structure of the heel spring 106 and keel spring 105 when the prosthetic heel strikes the ground surface during a walking or running gait cycle. A carbon-composite J-spring 107 attaches to the anterior aspect 108 of the carbon composite foot structure 104 and passes posteriorly through the ankle-bearing block 103 upwardly to its posterior-proximal end 109. A computer-controlled active element 110 connects via rotational bearing 111 to the posterior-proximal curved-spring end 109. The anterior end of the active element 110 connects to the shank shell 102 via rotational bearing 112. The computer-controlled active element is in series with J-spring 107 to form an ankle joint series-elastic actuator. The active element of the series-elastic actuator can take the form of the first active element embodiment (FIGS. 5A and B), the second active element embodiment (FIGS. 6A and B), the third active element embodiment (FIGS. 7A-D and FIGS. 8Aa-Ca and FIGS. 8Ab-Cb), or the fourth active element embodiment (FIG. 9A-D). The shank shell 102 also contains the onboard electronic board 113 and battery 114. The electronic board 113 comprises artificial computational elements such as micro-processors, as well as analog to digital converters, onboard sensors, and other electronic components known to those of ordinary skill in the art. The onboard sensors include, but are not limited to, accelerometers, rate gyros, joint angular sensors, an active element motor position sensor, and a temperature sensor. FIGS. 2a and b shows the components of the prosthesis without the surrounding shank shell 102.

Figure 3A:
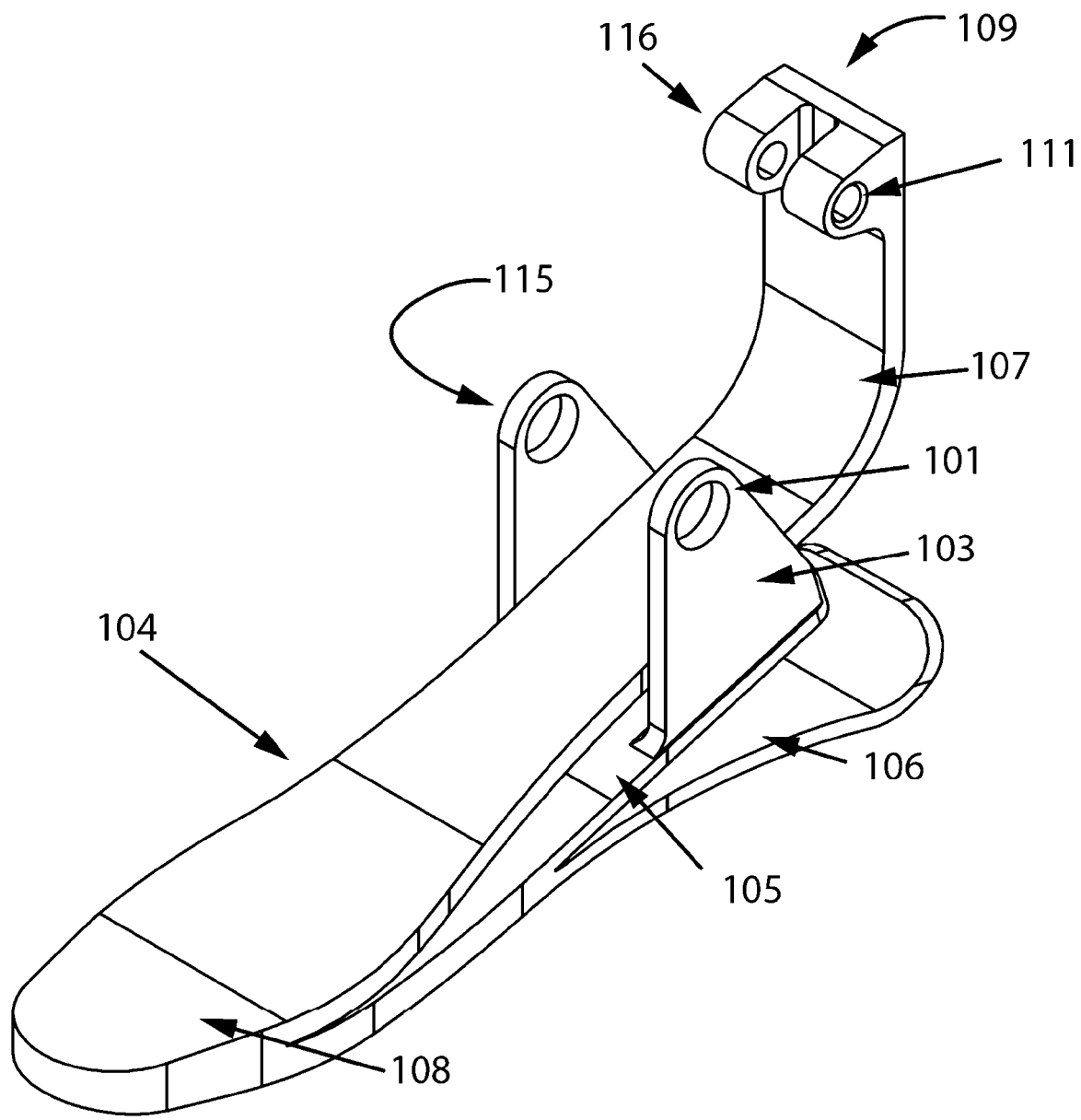
FIGS. 3a and b: Composite heel, keel, and J-spring structures.
Figure 3B:
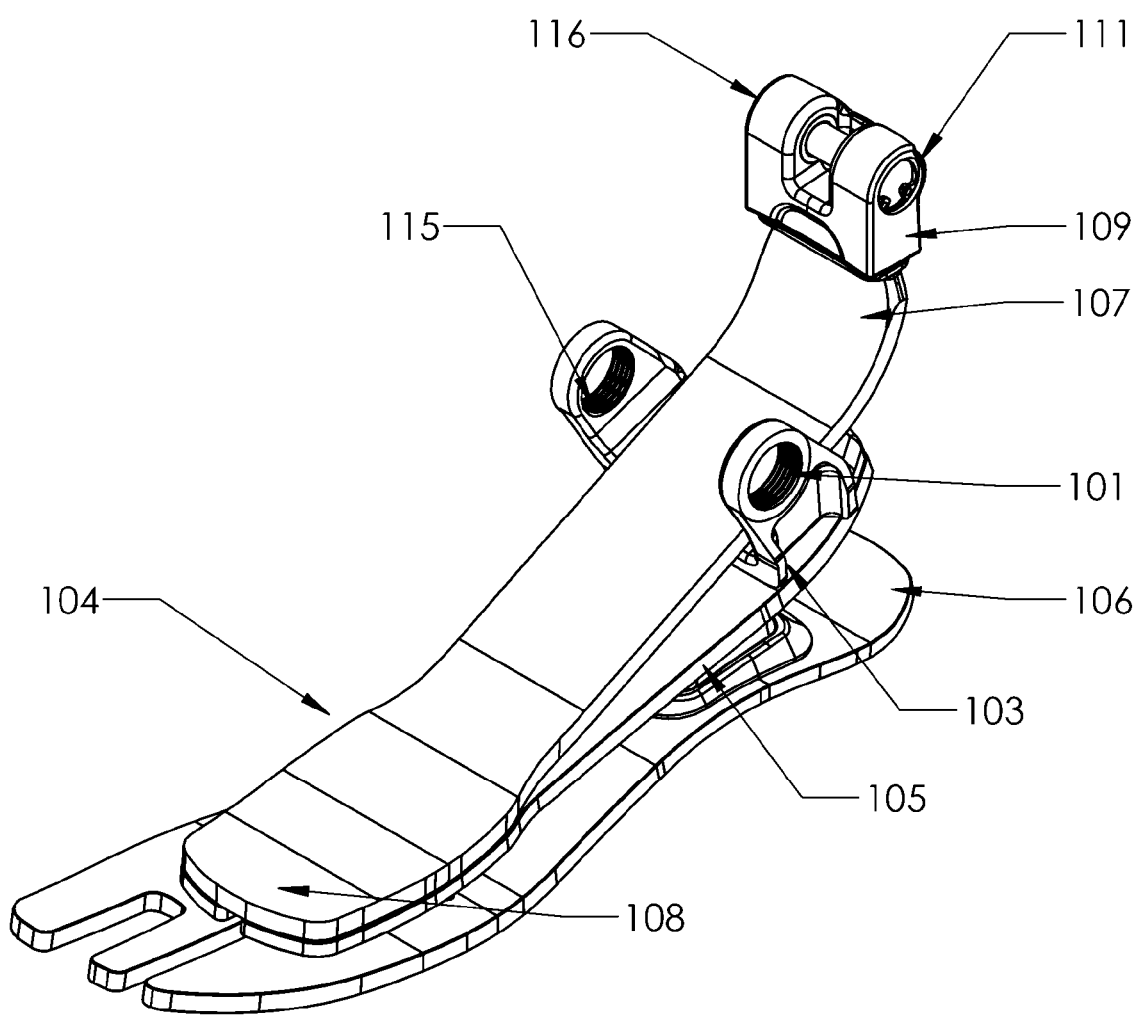
Figure 4A:
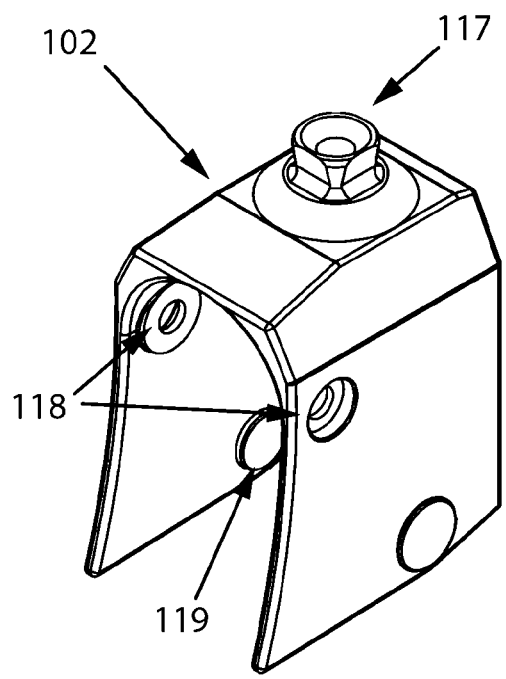
FIGS. 4a and b: Component shank shells.
Figure 4B:
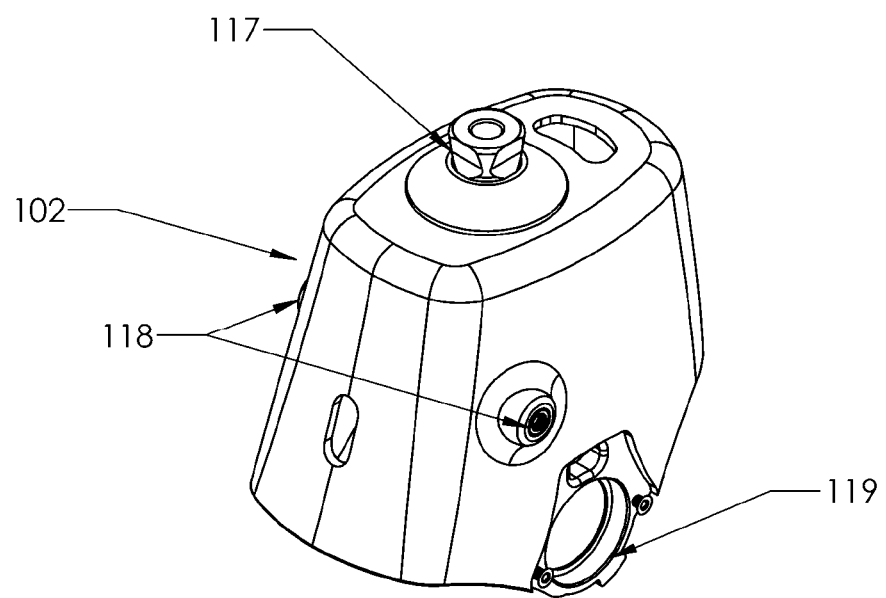

As in FIGS. 3a and b, the carbon composite foot structure 104 is made of keel spring 105 and heel spring 106. The components of the foot structure 105-106 are molded together, fastened, or bolted together at its anterior aspect 108 or along the keel length (shown). In addition, the carbon-composite J-spring 107 attaches to the anterior aspect 108 of the carbon composite foot structure 104 and passes posteriorly through the ankle-bearing block 103 upwardly to its posterior-proximal end 109. The anterior aspect of the J-spring 107 is bonded, bolted or fastened to the anterior aspect 108 of foot structure 104. The ankle bearing block 103 is bonded, bolted or fastened to the keel spring 105. Ankle bearing block 103 rotationally connects to the shank shell 102 via ankle bearing 101 that seats into access hole 115. The active element 110 shown in FIGS. 1 and 2 rotationally connects to the posterior-proximal end of series J-spring 107 via bearing 111 that seats into access hole 116. The shank shell component 102, shown in FIGS. 4a and b, connects to the user's prosthetic shank through a standard pyramid interface 117 and houses the active element 110, electronic board 113, and battery 114. Both the electronic board 113 and battery 114 are attached to the shank shell 102, while the anterior aspect of active element 110 pivots about bearing 112 imbedded into bearing access hole 118. The shank shell 102 also connects to the ankle bearing block 103, attached to the foot structure 104, at another bearing 101 imbedded into bearing access hole 119 to form the ankle joint.

Figure 10A:
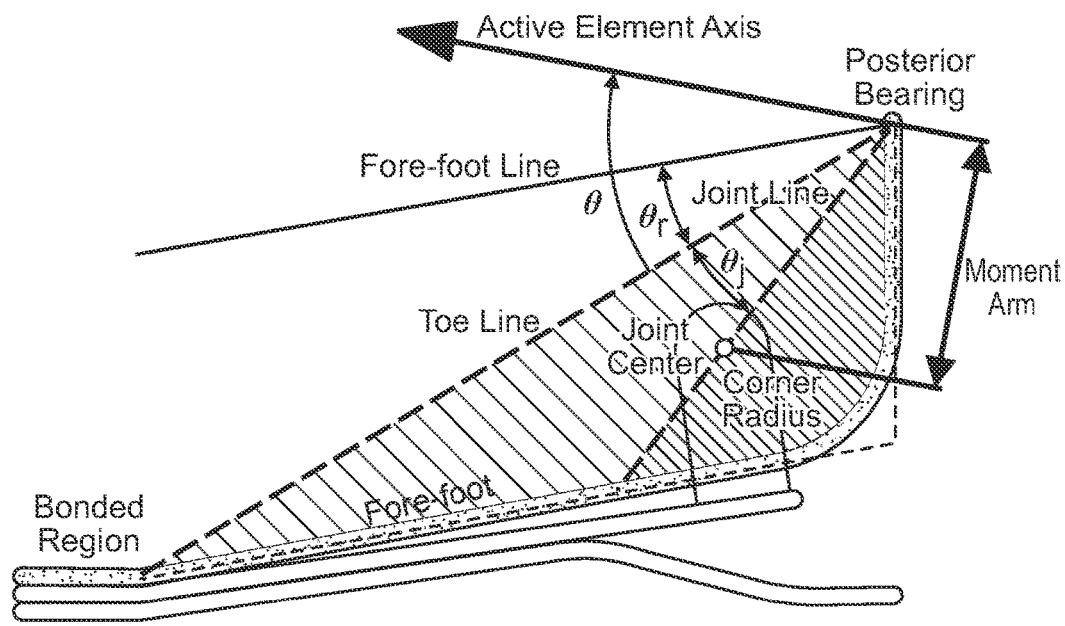
Figure 10B:
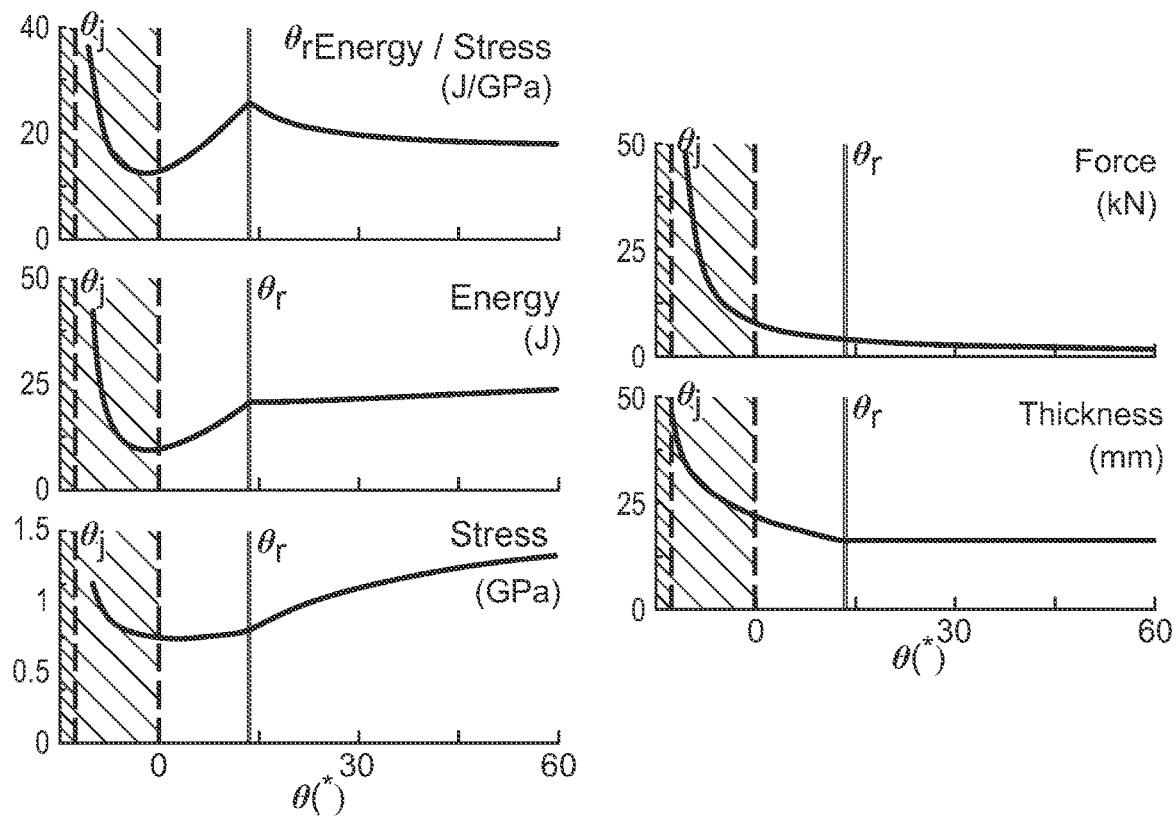

The active element 110 of the series-elastic actuator can take the form of the first active element embodiment 120 (FIGS. 5A and B), the second active element embodiment 124 (FIGS. 6A and B), the third active element embodiment 128/129 (FIGS. 7A-D and 8Aa-Ca and FIGS. 8Ab-Cb), or the fourth active element embodiment 155/156 (FIG. 9A-D). Each embodiment connects to the shell through the anterior bearing 112 as well. By attaching the active element 110 to the shell 102 and J-spring 107 through the bearing interfaces, 111 and 112, we prevent bending moments from occurring in the linear active element 110. All embodiments of the active element 110 are designed so that the line of action of the force between the active element 110 and the J-spring 107 does not pass through the active region of the J-spring 107 (negative active element angles in FIG. 10A-C). This condition ensures that the bending stress along the length of the spring is never zero. A comparison of the stressed spring from a force applied to the posterior pivot 109 parallel to the base of the spring and pointing at the base is shown in FIG. 10A-C.

Figure 5A:
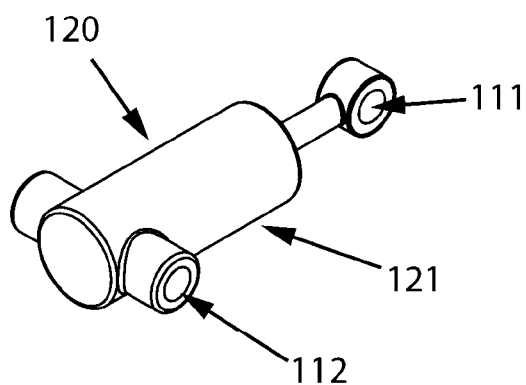
FIGS. 5A and B: First active element embodiment—Spring-parallel variable damper in perspective and cross-sectional views.
Figure 5B:
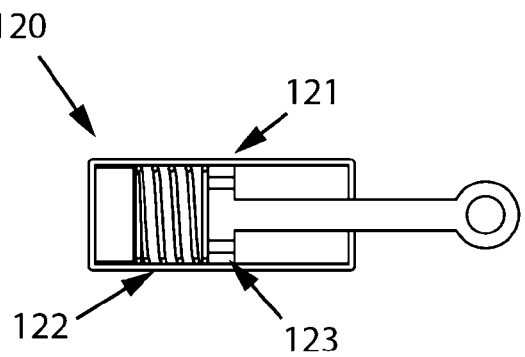

In a first active element embodiment 120, shown in FIGS. 5A and B, the active element comprises a computer-controlled damper 121 employing hydraulic, pneumatic or magnetorheological fluids with a parallel passive return spring 122. While there are non-zero ground-foot interaction forces during the stance phase of walking, the damping of the device can be controlled to allow the length of the first active element embodiment 120 to be modulated, in order to adjust the ankle equilibrium position, in an updating manner under microprocessor control. Through computer control of hydraulic valves 123 (or magnetorheological fluids), the damping of the device can be modulated to allow the ankle spring equilibrium position to change during operation. In a typical walking gait cycle, the damping can be reduced at heel strike to allow the ankle to plantar flex, and the active element to change length, during the controlled plantar flexion phase of stance, thereby changing the spring equilibrium ankle angle to a plantar flexed position near the gait transition from controlled plantar flexion to controlled dorsiflexion. At this point in the gait cycle, if the ground reaction force were eliminated, the ankle angle would assume a plantar flexed equilibrium posture with the keel 105, heel 106, and J-spring 107 elastic structures in equilibrium.

Near the gait transition from controlled plantar flexion to controlled dorsiflexion, the active element damping would then be maximized under computer control in order to maintain the active element length, and the corresponding equilibrium angle of the ankle joint, at the same plantar flexed posture such that, at the exact moment of toe-off, the ankle joint would assume a plantar flexed posture. Hence, under computer-controlled modulation of active element damping, the ankle-foot prosthesis of the first active element embodiment 120 can achieve an enhanced powered plantar flexion at push off.

During the early swing phase following toe-off, the active element damping would be minimized under computer control. If the first active element embodiment 120 comprises a hydraulic damper 121, the computer would send an electrical command to open the hydraulic valve 123 to enable maximal fluid flow and minimal fluid resistance. In distinction, if the first active element embodiment 120 comprises a magnetorheological damper, the computer would decrease the current through the damper's electromagnet to minimize the magnetic field passing through the magnetorheological fluid, so as to minimize effective damping.

Such a low active-element damping would enable the light spring 122 in parallel with the damper 121 to return the active element length, and consequently the ankle joint position 101, to a neutral posture, so as to enable foot clearance during the early swing phase of a walking gait cycle. Most typically, the neutral ankle position would be equal to approximately 90 degrees, or the angle between the longitudinal axis of the prosthetic pyramid 117 in FIG. 4, or the longitudinal axis of the shank, and the ground when the prosthesis rests on a flat surface.

Once the ankle joint 101 has returned to a neutral posture during the mid-swing phase, the onboard computer would increase damping levels once again in preparation for the next heel strike. This active element embodiment 120 would provide some control while keeping mass, energy, and noise to a minimum. However, the computer-controlled damper 121 would be unable to actively select optimal ankle equilibrium angles during the swing phase for various terrains.

Figure 6A:
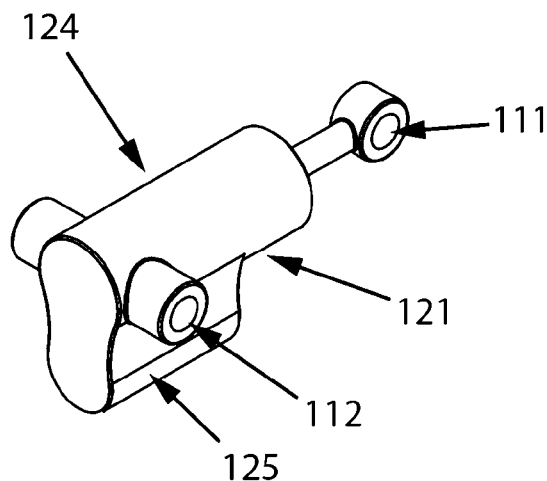
FIGS. 6A and B: Second active element embodiment—Motor-parallel variable damper in perspective and cross-sectional views.
Figure 6B:
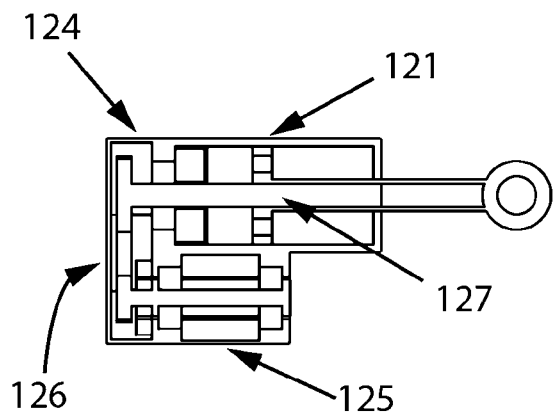
Figures 7A, 7B:
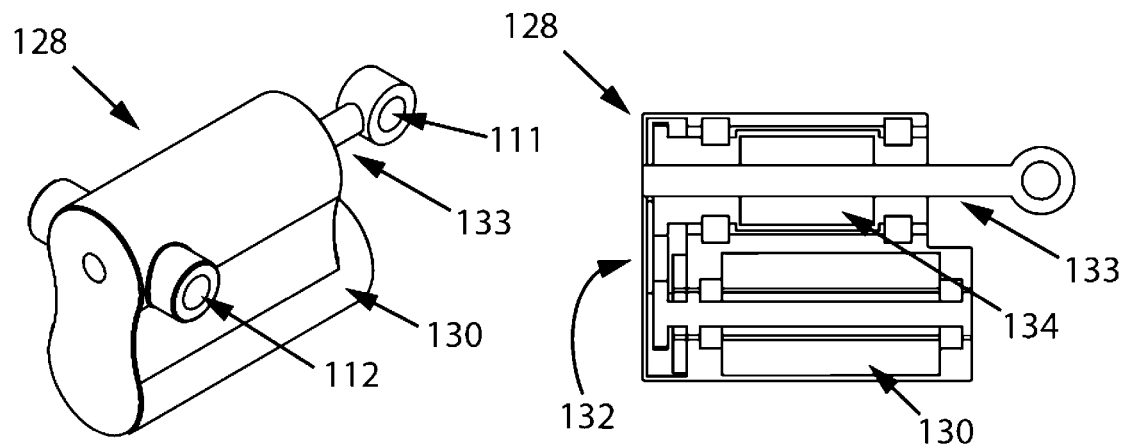
FIGS. 7A-D: Third active element embodiment—Indirect (A, B) or direct-drive (C, D) actuator screw embodiment in perspective (A, C) and cross-sectional (B, D) views.
Figures 7C, 7D:
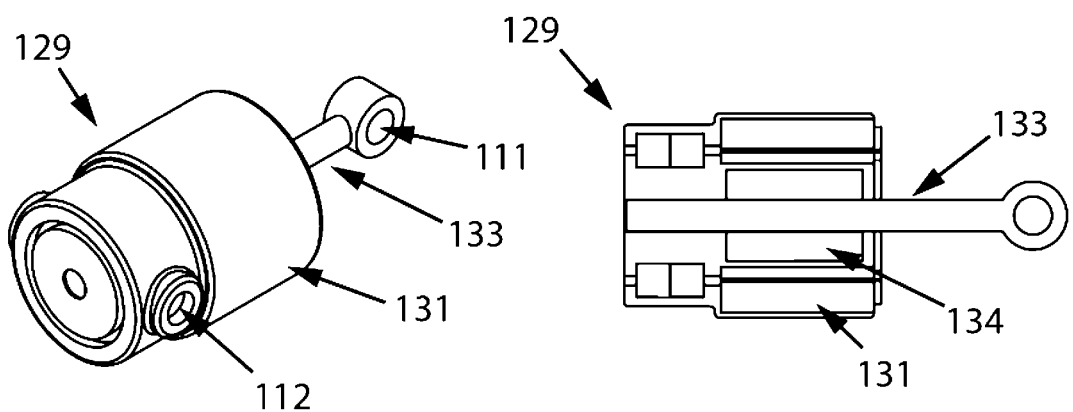

In the second active element embodiment 124 shown in FIGS. 6A and B, the active element comprises a computer-controlled damper 121 employing hydraulic, pneumatic or magnetorheological fluids. The computer-controlled damper 121 is operatively coupled to a small motor 125 via a belt or spur gear transmission 126 to enable the computer modulation of active element length, or ankle spring equilibrium, during the swing and stance phases of walking. During the swing phase, the damping level is minimized, and the motor is controlled by an onboard computer to adjust the length of the active element via internal screw 127 in order to set the spring equilibrium ankle angle to achieve foot clearance during the early swing phase, and an optimized foot orientation in preparation for foot-strike during the late swing phase. During stance, the motor turns off so as to minimize electrical power consumption, and the damping level is then modulated to control ankle impedance and spring equilibrium angle depending on gait phase, speed and underlying terrain.

Using this second active element embodiment 124, the ankle-foot device is capable of ankle spring equilibrium modulation in an updating manner across gait phase, walking speed, and terrain. For example, during the swing phase of a walking gait cycle, the damping level of the variable damper 121 under computer control would be minimized, and the small motor 125 would actively modulate the active element length, and consequently the ankle angle. Since the loads on the keel 105, heel 106, and J-spring 107 elastic structures are low during the swing phase, the modulated ankle angle by motor 125 (computer-controlled by computational chips on electronic board 113) would largely determine the ankle spring equilibrium position at each instant in time. During the early swing phase, the motor would actively dorsiflex the ankle joint 101 to achieve foot clearance. The magnitude of dorsiflexion during this early swing phase period would be modulated across walking speed and terrain in a manner that emulates biological ankle function.

Additionally, during the late swing phase period, the motor 125 would control the active element length, and consequently the ankle joint angle, to achieve a foot-strike spring equilibrium angle and posture that emulates the biological ankle. For example, for stair descent, the small motor 125 would actively plantar flex the ankle joint 101 during the late swing phase in preparation for fore-foot strike. At the first instant of fore-foot strike, the ankle joint 101 would then be plantar flexed with a plantar flexed spring equilibrium angle.

The second active element embodiment 124 can also provide spring equilibrium control during the stance phase of a walking gait cycle. Similar to the first active element embodiment 120, the second embodiment 124 would undergo damping control modulations to adjust the active element length, and the ankle spring equilibrium angle, at the transition from controlled plantar flexion to controlled dorsiflexion. In a typical level-ground walking gait cycle, the damping can be set to moderate levels at heel strike to allow the ankle to plantar flex, and the active element to change length, during the controlled plantar flexion phase of stance, thereby changing the spring equilibrium ankle angle from its neutral foot-strike posture to a plantar flexed position at the gait transition from controlled plantar flexion to controlled dorsiflexion. At this gait transition from controlled plantar flexion to controlled dorsiflexion, the active element damping would then be maximized under computer control in order to maintain the active element length, and the corresponding equilibrium angle of the ankle joint, at the same plantar flexed posture such that, at exact moment of toe-off, the ankle joint would assume a plantar flexed posture. Hence, under computer-controlled modulation of active element damping, the ankle-foot prosthesis of the second active element embodiment 124 can achieve an enhanced powered plantar flexion at push off.

The second active element embodiment 124 can also provide damping impedance control during the stance phase. For example, for stair descent, the small motor 125 would actively plantar flex the ankle joint 101 during the late swing phase in preparation for fore-foot strike. At the first instant of fore-foot strike, the ankle joint 101 would then be plantar flexed with a plantar flexed spring equilibrium angle. To effectively emulate biological ankle function during this early stance period of stair descent, an impedance damping control would be initiated. The small motor 125 would be turned off, and the damping from the variable damper 121 would be modulated under computer control to smoothly lower the prosthetic heel spring 106 slowly to the stair tread surface.

One limitation of the second active element embodiment 124 is that, due to its small motor size, net positive work will be zero during stance, and therefore below biomimetic levels during the powered plantar flexion phase of walking.

In the third active element embodiment 128/129 shown in FIGS. 7A-D, the active element comprises an electric motor 130/131 connected indirectly (e.g. using a belt 132) or directly to a ball, roller, or lead screw 133 and nut 134. The belt driven embodiment 128 contains a brushed or brushless dc motor 130 in parallel to a ball screw, roller screw, or lead screw 133. The motor is connected to either the nut 134 or screw 133 using a belt transmission 132. The direct drive linear actuator 129 contains a roller, ball, or lead screw 133 and nut 134 in line with the axis of the motor 131. The motor 131 is a brushless or brushed dc motor and can be designed to allow the screw 133 to pass through the center. The motor 131 is directly attached to the nut 134 or screw 133. In both cases, spring potential energy can be stored in the J-spring by rotating the shell 102 about the ankle joint 101 using the body weight of the user or through rotation of the motor 128/129, causing a linear motion between the screw 133 and nut 134 that pushes or pulls on the posterior pivot 111 of the J-spring 107.

The pitch of the screw is adjusted to achieve nonbackdriveability or semi-backdriveability, so as to minimize electrical power consumption during those times when J-spring 107 and foot structure (keel and heel springs) 104 enables proper dynamics, and the active element need not change length. During the swing and stance phases, the active element 128/129 is controlled to adjust the distance between the posterior pivot 111 and the anterior pivot 112 in order to set the spring equilibrium ankle angle to achieve foot clearance during the early swing phase, an optimized foot orientation in preparation for foot-strike during the late swing phase, and a plantar flexion ankle angle at toe-off. Using this third active element embodiment 128/129, the ankle-foot device 100 is capable of ankle spring equilibrium modulation in an updating manner across gait phase, walking speed, and terrain. Additionally, the third active element embodiment 128/129 can also provide powered plantar flexion with net mechanical work during the late stance period of walking. One limitation of the third active element embodiment 128/129 is the nonbackdriveability or semi-backdriveability of the screw transmission, making it difficult to achieve high bandwidth closed-loop force or impedance control at high electrical power efficiency.

Figures 8A, 8B:
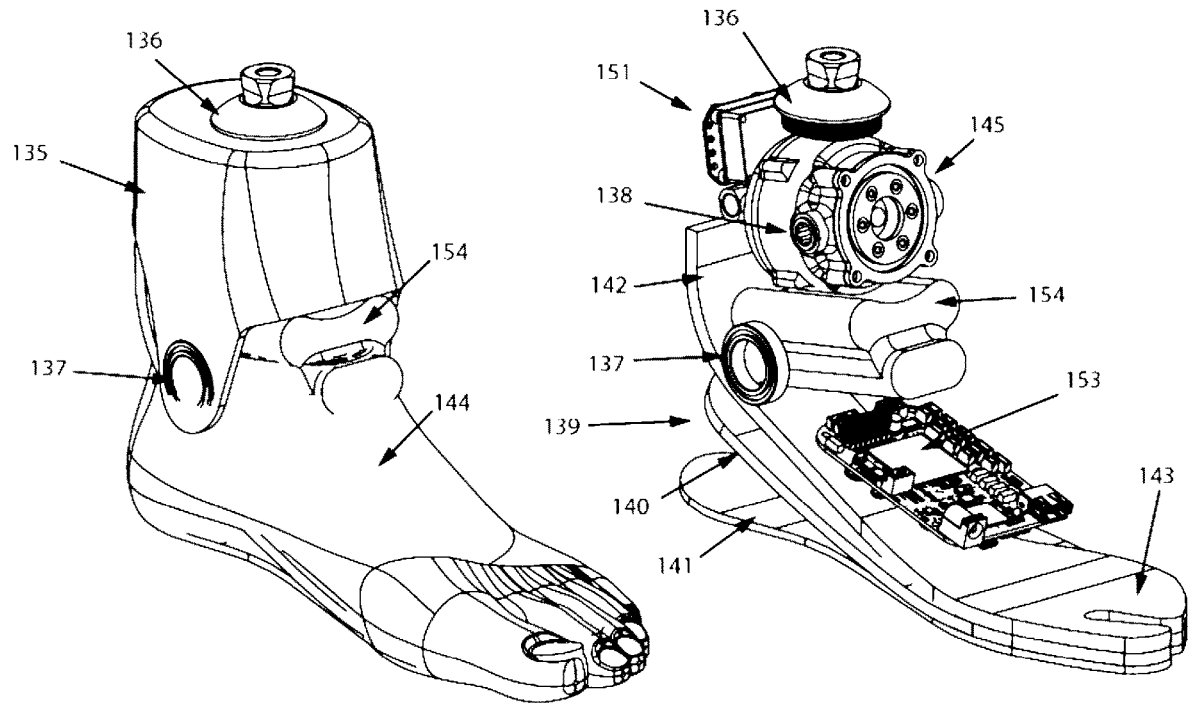
FIGS. 8Aa-Cb: Detailed design for active-element embodiment three with a direct drive.
Figure 8C:
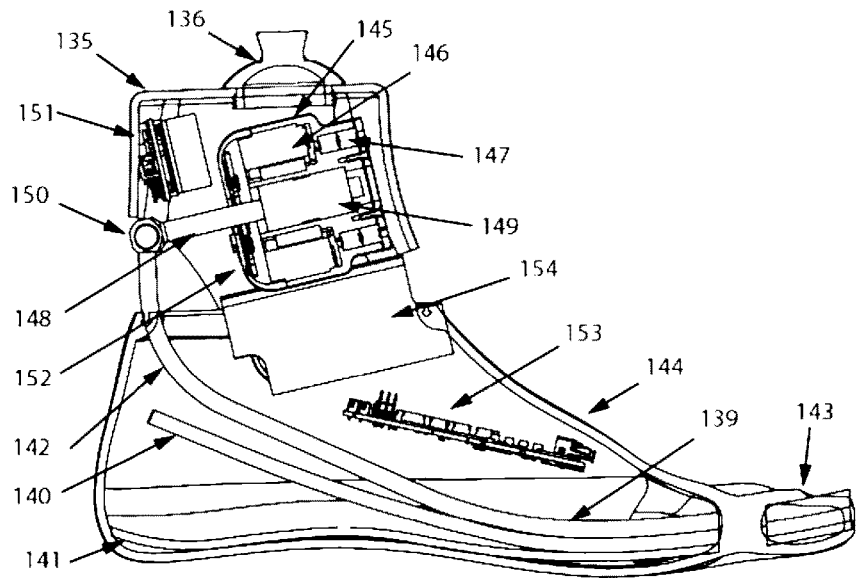
Figure 8A:
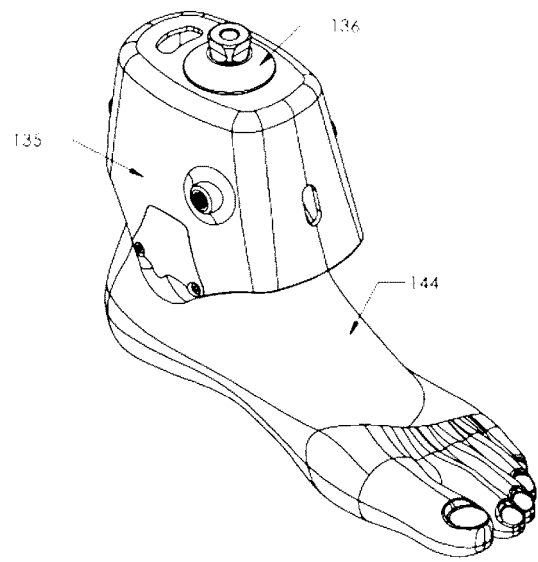
Figure 8B:
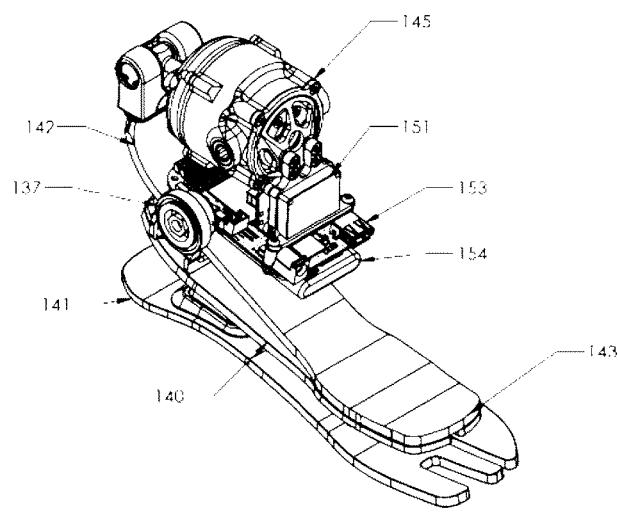
Figure 8C:
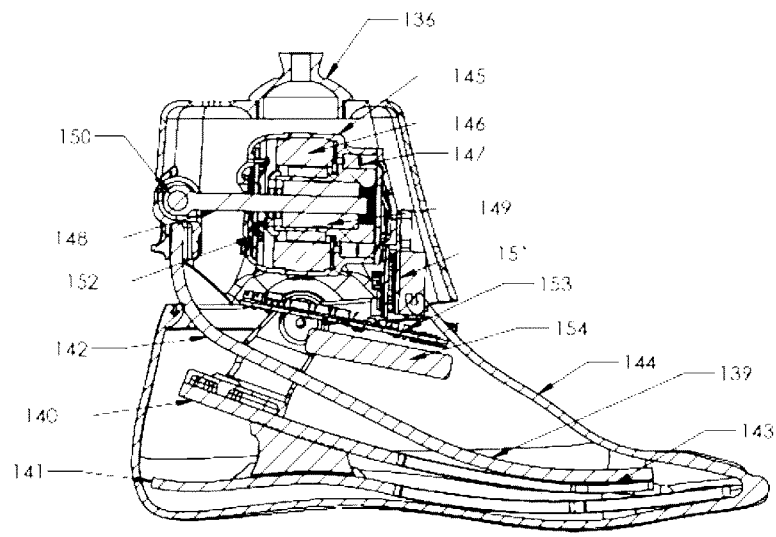
Figures 9A, 9B:
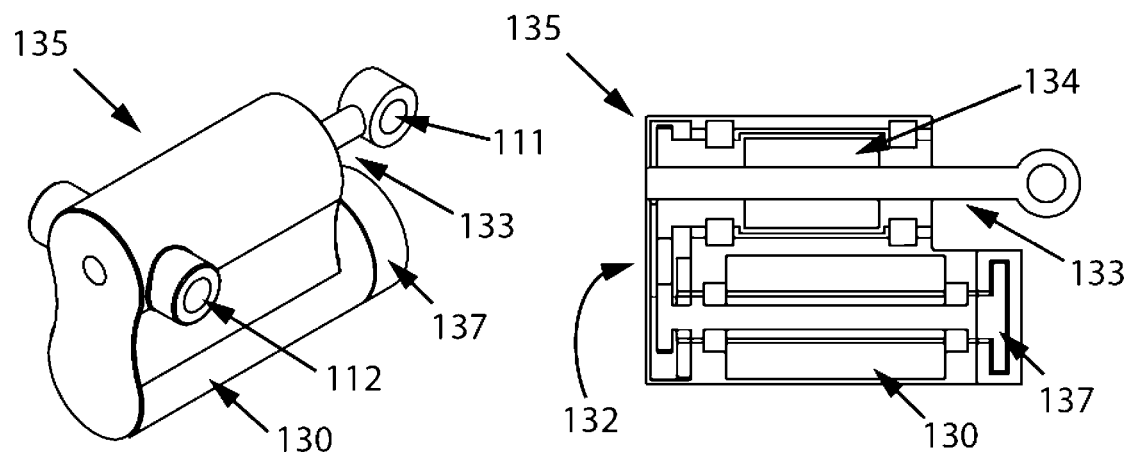
FIGS. 9A-D: Fourth active element embodiment—Clutchable indirect (A, B) or direct-drive (C, D) actuator screw embodiment.
Figures 9C, 9D:
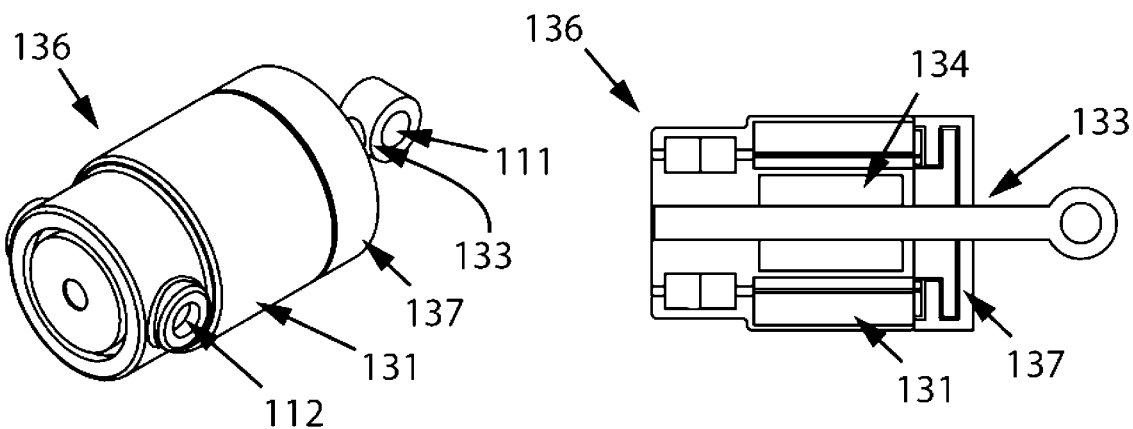

To mitigate these challenges, in a preferred embodiment shown in FIGS. 8Aa-Ca and FIGS. 8Ab-Cb, the transmission of the third active element embodiment would comprise a roller screw to enable high transmission ratio through a small screw lead, ø, (e.g. ø within the range of 0.5 mm≤ø≤2.5 mm), but at an increased transmission efficiency (~70% to 90%) compared to ball and lead screw transmissions (~20% to 70%)).

Shown in FIG. 8 is a detailed version of the invention with active-element embodiment 3 comprising the direct drive architecture. Here, the active element is encased in an aluminum shell 135 which comprises the pyramid attachment point 136, joint center bearing 137, and internal anterior bearing 138. The carbon composite spring structure 139 is made up of a keel spring 140, heel spring 141, and a J-spring 142 optimized for a size 27 foot. These are all attached via an anterior bonded region 143 and housed within a cosmetic foot shell 144. The active element comprises an aluminum housing 145, a T-motor RI50 motor 146, a set of angular contact bearings 147, and a 7 mm diameter, 2 mm lead roller screw 148 and nut 149. The roller screw 148 has a posterior bearing 150 that interfaces with the J-spring 142. The electronics shown comprise an Ingenia motor driver 151, a motor encoder 152, and a Beagle Bone computational board 153. This system is powered by a custom five cell lithium polymer battery pack 154.

In the fourth active element embodiment shown in FIGS. 9A-D, the active element 135/136 comprises the same elements as the third active element embodiment, with the addition of a clutch, or variable-damper component 137, that acts on the motor shaft. The clutch, or variable-damper 137 offers a low electrical power strategy to lock the motor shaft, or active element length, when the passive-elastic series J-spring 107 and foot structure (keel and heel springs) 104 enable proper dynamics during the stance phase. Because the clutch/variable-damper 137 offers this capability, the ball, roller, or lead screw 133 need not be non-backdriveable or semi-nobackdriveable. Thus, the indirect 130 or direct-drive motor 131 and screw 133 can be backdriveable to enable a high bandwidth closed-loop force control and/or impedance control. Using this fourth active element embodiment, the ankle-foot device 100 is capable of ankle impedance and ankle spring equilibrium modulation in an updating manner across gait phase, walking speed, and terrain. Additionally, the fourth active element embodiment can also provide powered plantar flexion with net mechanical work during the late stance period of walking.

The series-elastic actuator, comprising the series J-spring 107 and an active element 110, is designed to maximize energy storage. In one embodiment of the present invention, the ankle-foot prosthesis 100 is designed such that, at peak ankle dorsiflexion, the Active Element Axis is approximately located at, or above, the Fore-foot Line, with an active element angle equal to, or greater than, the angle spanning from the Toe Line to the Fore-foot Line (See FIGS. 10A-C for details). In a preferred embodiment, the ankle-foot prosthesis is designed such that, at peak ankle dorsiflexion, the Active Element Axis is approximately in line with the Fore-foot Line, with a positive active element angle corresponding to that angle spanning from the Toe Line to the Fore-foot Line. Such a design is a preferred embodiment because it is at these geometries that the series spring energy storage capacity per unit spring stress is maximized. To maximize energy storage per unit spring mass, ideally the curved-spring is made of carbon composite, but could also be made of other elastic materials such as fiberglass or titanium.

FIG. 10A is a J-spring diagram for various active element angles. The Active Element Axis defines the direction of the force along the active element longitudinal axis. The direction of the axis is defined by the active element angle, $\theta$, measured from the Toe Line. The Toe Line connects the Posterior Bearing to the posterior edge of the Bonded Region. The Joint Line connects the Joint Center to the Posterior Bearing. The Fore-foot Line is through the Posterior Bearing and parallel to the flat section of the Forefoot. FIG. 10B shows the results of the simulation with $\theta$ ranging from $-10°$ to $60°$ ($-0.17$ to $1.05$ radians). Each plot displays the Joint Line, Toe Line, and the Fore-foot Line. Energy per unit stress is maximized for a feasible design when the Active Element Axis is colinear with the Fore-foot Line, $\theta=\theta_F$. FIG. 10C description of the simulation set up. The diagram shows the position (horizontal, vertical), of the ankle Joint Center, the posterior edge of the Bonded Region at the toe, the end of the Fore-foot (corner radius is assumed to be zero), and the Posterior Bearing. The diagram is not to scale but all numbers displayed reflect those used for the plots in B). Also shown are the constants, variables, and relationships used in the simulation. The simulation assumes a constant ankle Joint Torque, Quasi-Stiffness, Modulus of Elasticity, and Spring Width. The moment arm is the perpendicular distance between the Joint Center and the Active Element Axis, a function of $\theta$, $f_r(\theta)$. The active element Force is calculated using Joint Torque and the Moment Arm. The thickness is calculated as a function of $\theta$, $f_h(\theta)$, by keeping the Joint Angle, $\alpha$, constant. The Fore-foot and the posterior section of the spring are assumed to be of constant thickness with a rectangular cross-section and undergo beam bending deformation to produce the Joint Angle rotation, $\alpha$. Simulation assumes small angle approximation and therefore results are approximate.

The J-spring has been designed to maximize energy storage while keeping mass and peak stress to a minimum in a low-profile package. The design of the spring can be best understood through FIGS. 1-3 and the diagrams and simulation results shown in FIGS. 10A-C. The J-spring is attached at its anterior end to the anterior toe region of the prosthetic foot keel spring. The concave-up J-spring then passes through the ankle bearing block attached to the posterior aspect of the prosthetic foot keel spring, continuing upwardly to the J-spring's posterior-proximal end. Assuming a generally vertical orientation, this posterior-proximal end of the J-spring is attached via the posterior bearing to the in-series, computer-controlled active element.

From the posterior active element bearing, we can define the Active Element Axis as the line that generally passes through the longitudinal axis of the active element (See FIG. 10A). We define the direction of the Active Element Axis as the active element angle, $\theta$, measured from the Toe Line: the line that connects the posterior edge of the bonded region to the posterior active element bearing. The Fore-foot Line is the line that passes through the posterior active element bearing and generally parallel to the fore-foot of the J-spring. The fore-foot is defined as the relatively straight portion of the spring between the bonded region and the corner radius. The Joint Line connects the ankle joint center of the prosthesis to the posterior active element bearing.

For the simulation results shown in FIG. 10B, the J-spring is constructed from carbon fiber, and its dimensions are based upon biological foot geometry. In the simulation, we apply a constant torque (120 Nm) and quasi-stiffness (292 Nm/rad) about the ankle joint center consistent with biological peak torque and peak dorsiflexion angle taken from biomechanical gait data of a 72 Kg person walking with intact biological legs. The quasi-stiffness of the joint is defined as the ratio of the peak dorsiflexion torque applied about the ankle over the peak dorsiflexion angle. In simulation, we vary the angle between the Active Element Axis at peak dorsiflexion and the Toe Line, referred to herein as the active element angle, $\theta$. The Fore-foot line is located at $\theta_F$ above the Toe Line and the Joint Line is located at $\theta_J$ below the Toe Line. The torque is computed by multiplying the force applied by the Active Element along the Active Element Axis by the perpendicular distance from the ankle joint rotational center to the Active Element Axis. This distance, referred to as the moment arm, changes along with the force output of the Active Element as the active element angle $\theta$ changes. Also, since the quasi-stiffness of the joint is based on the bending stiffness of the spring (which is proportional to the cube of the spring thickness), the thickness of the spring changes with $\theta$ as well. Further description of the simulation is presented in FIG. 10C.

For the simulation results of FIG. 10B, energy is defined as the strain energy stored in the J-spring, stress is the peak bending stress along the J-spring, force is the force produced in the active element, and thickness is the uniform thickness of the J-spring. While in practice the J-spring can have a non-uniform thickness to evenly distribute stress throughout the spring, the simulation assumes uniform thickness for simplicity. At the point of maximum ankle dorsiflexion, the energy storage capacity, peak stress, and energy storage capacity/unit peak stress of the J-spring are all minimized when the Active Element Axis is approximately in line with the Toe Line ($\theta \approx 0$). Energy storage approaches infinity as $\theta$ becomes negative and the Active Element Axis approaches the Joint Line ($\theta \to \theta_J$); however, this is due to force and peak stress increasing to infinity as well. Such an applied force by the active element would be impractical for a physical device. In distinction, for positive values of the active element angle $\theta$, energy storage capacity increases as $\theta$ increases, but with increases in peak stress in the J-spring. Hence, for a practical device, the active element angle $\theta$, should be positive throughout operation.

At peak ankle dorsiflexion, the energy storage per unit stress is maximized, and the thickness of the spring is minimized when the Active Element Axis points approximately along the Fore-foot Line ($\theta \approx \theta_F$). As shown in FIG. 10B, an optimized elastic structure for a 72 Kg person offers a substantial series elasticity to the active element. By keeping the angle of the Active Element Axis at or above the Fore-foot Line ($\theta \geq \theta_F$), total energy storage capacity ranges from 20 Joules to 26 Joules. Hence, in one embodiment of the present invention, the ankle-foot prosthesis is designed such that, at peak ankle dorsiflexion, the Active Element Axis is approximately located at, or above, the Fore-foot Line, with an active element angle equal to, or greater than, the angle spanning from the Toe Line to the Fore-foot Line. In a preferred embodiment, the ankle-foot prosthesis is designed such that, at peak ankle dorsiflexion, the Active Element Axis is approximately in line with the Fore-foot Line, with a positive active element angle corresponding to that angle spanning from the Toe Line to the Fore-foot Line ($\theta \approx \theta_F$). Such a design is a preferred embodiment because the series spring energy storage capacity per unit spring stress is maximized.

Depending on the functionality sought, the design of the active element can take the form of one of four embodiments noted above. In the first active-element embodiment, the active element comprises a computer-controlled damper employing hydraulic, pneumatic or magnetorheological fluids with a parallel-passive return spring. Through computer control, the damping of the device can be modulated to allow the ankle spring equilibrium position to change during operation. For example, for a typical level-ground walking gait cycle, the damping can be adjusted at heel strike to allow the ankle to plantar flex, and the active element to change length, during the controlled plantar flexion phase of stance, thereby changing the spring equilibrium ankle angle from a neutral position at heel strike to a plantar flexed position near the gait transition from controlled plantar flexion to controlled dorsiflexion. At this point in the gait cycle, if the ground reaction force were eliminated, the ankle angle would assume a plantar flexed posture at spring equilibrium. Near this gait transition from controlled plantar flexion to controlled dorsiflexion, the active element damping would then be maximized under computer control in order to maintain the equilibrium angle of the ankle joint at the same plantar flexed posture such that, at toe-off, the ankle is plantar flexed. Hence, through active element damping modulation during early to mid-stance, the toe-off ankle spring equilibrium angle can be controlled, or the degree to which the ankle plantar flexes throughout terminal-stance powered plantar flexion. The percent gait cycle at which the damping is modulated from relatively moderate damping to a relatively high level of damping, locking the active element length and establishing the ankle spring equilibrium angle, can occur during early stance controlled plantar flexion, or during the controlled dorsiflexion gait phase, depending on walking speed and underlying terrain.

During the early swing phase following toe-off in level-ground walking, the active element damping can be minimized under processor control to allow the light spring to return the ankle joint, and the active element, to a neutral position, preventing the toe from hitting the ground. Once the ankle has returned to a neutral posture (approximately 90 degrees between the prosthetic shank and the ground when the prosthesis rests on a flat surface) during the mid-swing phase, the onboard computer would increase damping levels in preparation for the next foot strike. This embodiment would provide some control while keeping mass, energy, and noise to a minimum. However, the computer-controlled damper would be unable to actively select optimal equilibrium angles during the swing phase to provide biomimetic dynamics across varied terrain surfaces.

In the second active-element embodiment, rather than being coupled to a parallel spring, the computer-controlled damper is operatively coupled to a small motor to enable the computer modulation of active element length, or ankle spring equilibrium, during the swing and stance phases of walking. During the swing phase, the damping level is minimized, and the motor is controlled to adjust the length of the active element in order to set the spring equilibrium ankle angle to achieve foot clearance during the early swing phase, and an optimized foot orientation in preparation for foot-strike during the late swing phase. During stance, the motor is turned off under computer control so as to minimize electrical power consumption, and the damping level is then modulated to control ankle impedance and spring equilibrium angle depending on gait phase, speed and underlying terrain. Using this second embodiment, the ankle-foot device is capable of ankle spring equilibrium modulation in an updating manner across gait phase, walking speed, and terrain. Additionally, the second active element embodiment can also provide damping impedance control during the stance phase. One limitation of the second active element embodiment is that, due to its small motor size, net positive work will be below biomimetic levels during the powered plantar flexion phase of walking.

In the third active-element embodiment, the active element comprises an electric motor connected directly or indirectly (e.g. using a belt) to a ball, roller, or lead screw. The pitch of the screw is adjusted to achieve nonbackdriveability or semi-backdriveability, so as to minimize electrical power consumption during those times when the passive-elastic curved series spring and foot structure (keel and heel springs) enables proper dynamics, and the active element need not change length. During the swing and stance phases, the motor is controlled to adjust the length of the active element in order to set the spring equilibrium ankle angle to achieve foot clearance during the early swing phase, an optimized foot orientation in preparation for foot-strike during the late swing phase, and a plantar flexion ankle angle at toe-off. Using this third embodiment, the ankle-foot device is capable of ankle spring equilibrium modulation in an updating manner across gait phase, walking speed, and terrain. Additionally, the third active-element embodiment can also provide powered plantar flexion with net mechanical work during the late stance period of walking. One limitation of the third active-element embodiment is the nonbackdriveability or semi-backdriveability of the screw transmission, making it difficult to achieve high bandwidth closed-loop force or impedance control.

In the fourth active-element embodiment, the active element comprises the same elements as the third active element embodiment, with the addition of a clutch, or variable-damper component, that acts on the motor shaft. The clutch, or variable-damper, offers a low electrical power strategy to lock the active element length when the passive-elastic curved series spring and foot structure (keel and heel springs) enable proper dynamics during the stance phase. Because the clutch/variable-damper offers this capability, the ball, roller, or lead screw need not be nonbackdriveable or semi-backdriveable. Thus, the indirect or direct-drive motor and screw can be highly backdriveable to enable a high fidelity closed-loop force control and/or impedance control at high transmission efficiency. Using this fourth embodiment, the ankle-foot device is capable of ankle impedance and ankle spring equilibrium modulation in an updating manner across gait phase, walking speed, and terrain. Additionally, the fourth active element embodiment can also provide powered plantar flexion with net mechanical work during the late stance period of walking at high transmission efficiency.

For this active ankle-foot prosthesis, the series-elastic actuator can be designed with a modular motor in order to provide the user with differing levels of assistance depending on the size of motor used, allowing it to act as a quasi-passive or active ankle-foot prosthesis. Here, modular means that the motor can be swapped out with a motor of a different size without having to modify any other ankle-foot component, and that such a modification can be performed efficiently without requiring a great deal of time and effort. For example, using a small motor and a nonbackdrivable or semi-backdrivable transmission (third active-element embodiment), the computer-controlled active element can provide only spring equilibrium control while in the swing phase. By increasing the motor size, spring equilibrium control can then be performed both during the swing phase and stance phase, enabling net mechanical work and plantar flexion at toe-off. Thus, by swapping out the small motor in the third active element embodiment, the ankle-foot prosthesis can be converted from a quasi-passive prosthesis to a fully powered prosthesis. In this way, each of the active-element embodiments each have advantages and disadvantages in terms of device functionality.

We define five control embodiments corresponding to distinct prosthetic functionalities. The first control embodiment uses controlled damping (physical or virtual) and body weight to modulate the ankle spring equilibrium position during stance and swing but has no motor position control. The second control embodiment uses a motor to enable free-space, spring-equilibrium control but only during the swing phase, whereas the third control embodiment enables spring equilibrium control for both the swing and stance phases, but without net positive mechanical work during stance powered plantar flexion. These embodiments would be able to approximate the biomechanics of walking at a slow pace. The fourth control embodiment enables spring equilibrium ankle control for the swing and stance phases, and a biomimetic level of net positive mechanical work during the powered plantar flexion phase of walking. The fifth control embodiment enables the control functionalities of the fourth control embodiment, with the additional capability of closed-loop ankle impedance control during the stance phase. This capability would allow for biological torques throughout stance as well as virtual damping for shock absorption at foot strike, or slow descent of stairs, for example.

These control embodiments are made possible through a microprocessor board with a suite of intrinsic (on prosthesis) and extrinsic (off prosthesis) sensors. Intrinsic sensors comprise inertia measurement units (IMUs), joint and motor encoders, force sensors, and radio frequency or time of flight distance sensors. Extrinsic muscle sensors comprise, for example, electromyography, magnetomicrometry, and mechanomyography sensors. These intrinsic and extrinsic sensors are used to inform the microprocessor of the phase of gait, the terrain, and the intention of the user. For example, in a typical walking gait, heel strike is detected using a force sensor on the J-spring, or by using an internal model of the series spring system and the difference between the motor encoder and the joint encoder to estimate the force applied by the J-spring. The controller can then use encoder data, as well as IMU data, to determine when the foot is flat on the ground, and when peak dorsiflexion is reached based on the change in sign of the ankle joint velocity. These sensors can similarly be used to determine when the foot leaves the ground and signify the start of the swing phase. The microprocessor can also determine the terrain through data from distance sensors or using an onboard IMU and encoder data to calculate the ground slope and swing position of the foot using inertial signal integration and zero-velocity update calculations. With the addition of extrinsic electromyographic electrodes, muscle magnetomicrometry, or mechanomyography sensing, position control and push-off power could also be modulated based on input signals from the user's muscles.

The first active-element embodiment is capable of reproducing the first control embodiment. The second active-element embodiment is capable of both the first, second, and third control embodiments. In addition to the first, second, and third control embodiments, the third active-element embodiment is also capable of the fourth control embodiment. The fourth active-element embodiment is capable of all five control embodiments. It would be obvious to a person of ordinary skill in the art that the invention described herein could be used for any robotic ankle-foot device application, including prostheses, orthoses, exoskeletons or humanoid robotics.

Figure 11:
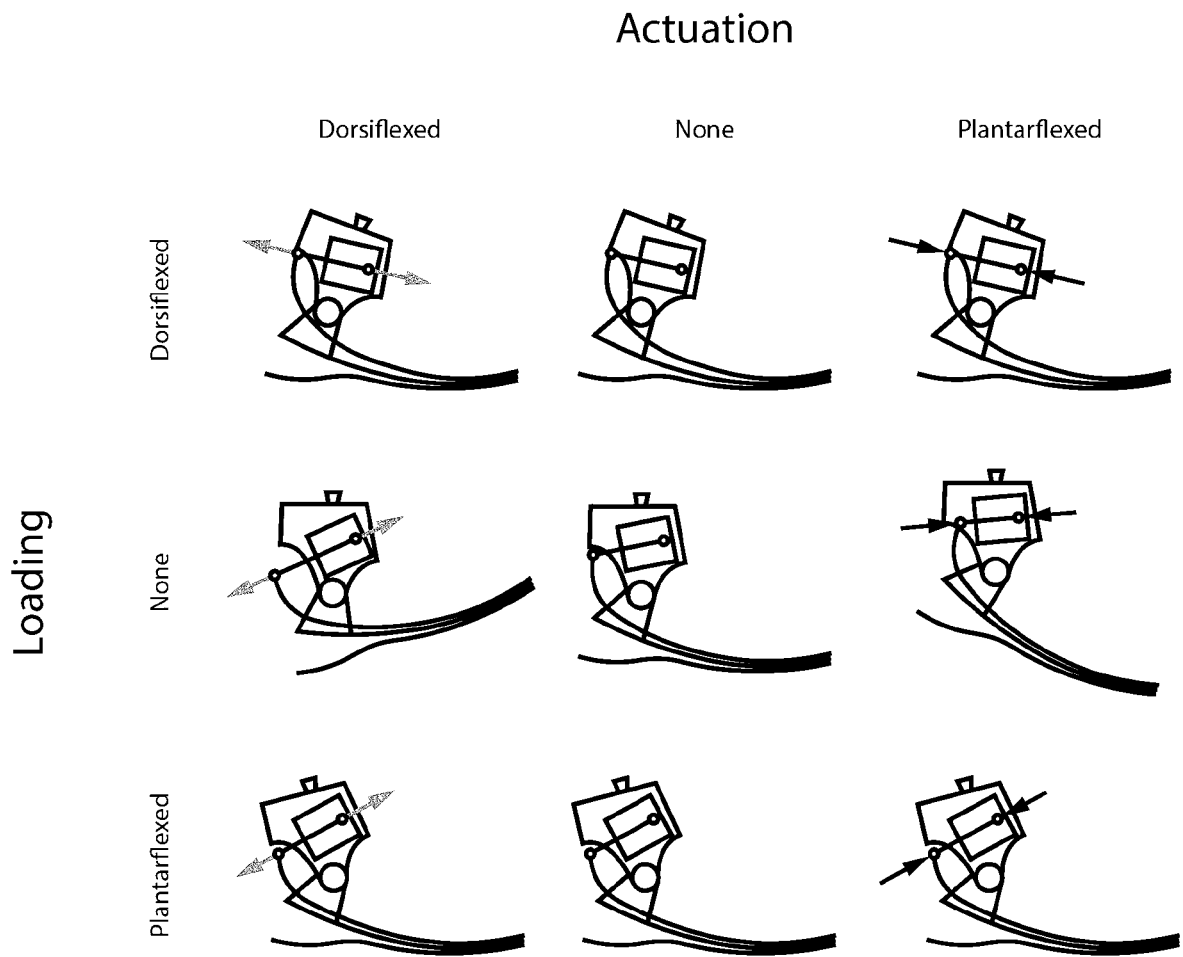
FIG. 11: Potential states of the series elastic actuator.

As noted above, the control of the ankle-foot prosthesis 100 with series J-spring actuation can take the form of five different control embodiments (see FIG. 12) depending on the level of assistance, size and design complexity of the active element being provided. FIG. 11 shows the possible states of the series elastic actuator that occur in each of the control embodiments. The series elastic actuator can be loaded in plantarflexion and dorsiflexion while on the ground. Under no load (None) when the ankle-foot prosthesis is off the ground, the actuator is capable of dorsiflexing the ankle joint by extending the active element length, and plantarflexing the ankle joint by shortening the active element length. Whether the ankle-foot prosthesis is off the ground or on the ground, the active element length is decreased to adjust the ankle spring equilibrium to a more plantarflexed position, or the active element length is increased to adjust the ankle spring equilibrium to a more dorsiflexed position.

Figure 12:
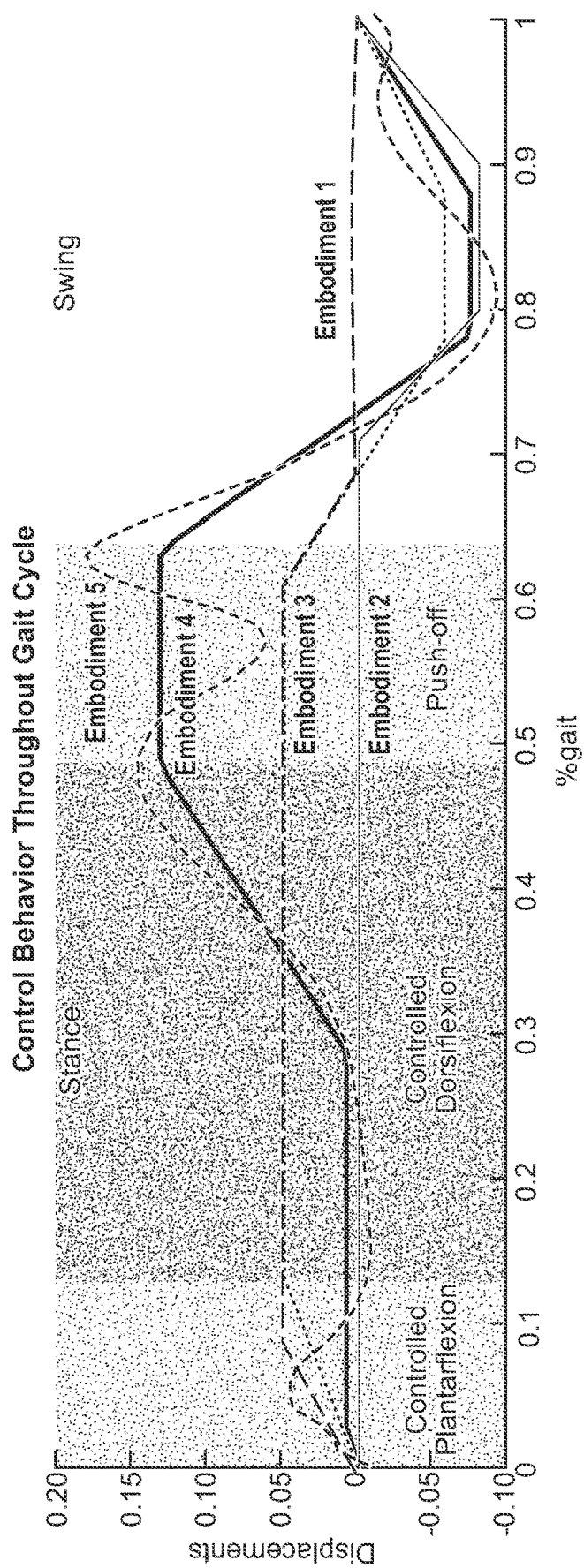
FIG. 12: Level-ground walking control behavior for the control embodiments. 44

FIG. 12 shows the angular position of the active element, which defines the ankle spring equilibrium position for all control embodiments, during a typical level-ground walking gait for the first control embodiment, second control embodiment, third control embodiment, fourth control embodiment, and fifth control embodiment. Shown here is level-ground walking with a stance spring-equilibrium ankle angle equal to 0° (0 radians), the value of the prosthesis joint angle at heel strike (% gait=0) and toe-off (% gait≈0.64). The walking gait is divided into stance (when the prosthesis is in contact with the ground) and swing (when the prosthesis is in the air) phases. The stance phase is subdivided further into three phases: Controlled Plantarflexion, which starts when the heel strikes the ground and lasts until the forefoot makes contact; Controlled Dorsiflexion, which starts when the forefoot makes contact and lasts until the ankle reaches maximum dorsiflexion; Push-off or Powered Plantar Flexion, which starts at peak dorsiflexion and ends when the toe leaves the ground. These phases are displayed in FIG. 12 with plantarflexion (pointing the toe) shown as positive while dorsiflexion (raising the toe towards the shank) is negative.

FIG. 13 through FIG. 17 show the operation of the prosthesis 100 throughout a walking gait and compares the resulting prosthesis joint to a typical biological ankle joint for each control embodiment. The actuator angular displacement in each figure is the same as shown in FIG. 12, and the spring displacement is based on biological ankle torques and an optimized spring. The prosthesis joint angle is calculated as the sum of the actuator angle and the spring angle.

Figure 13:
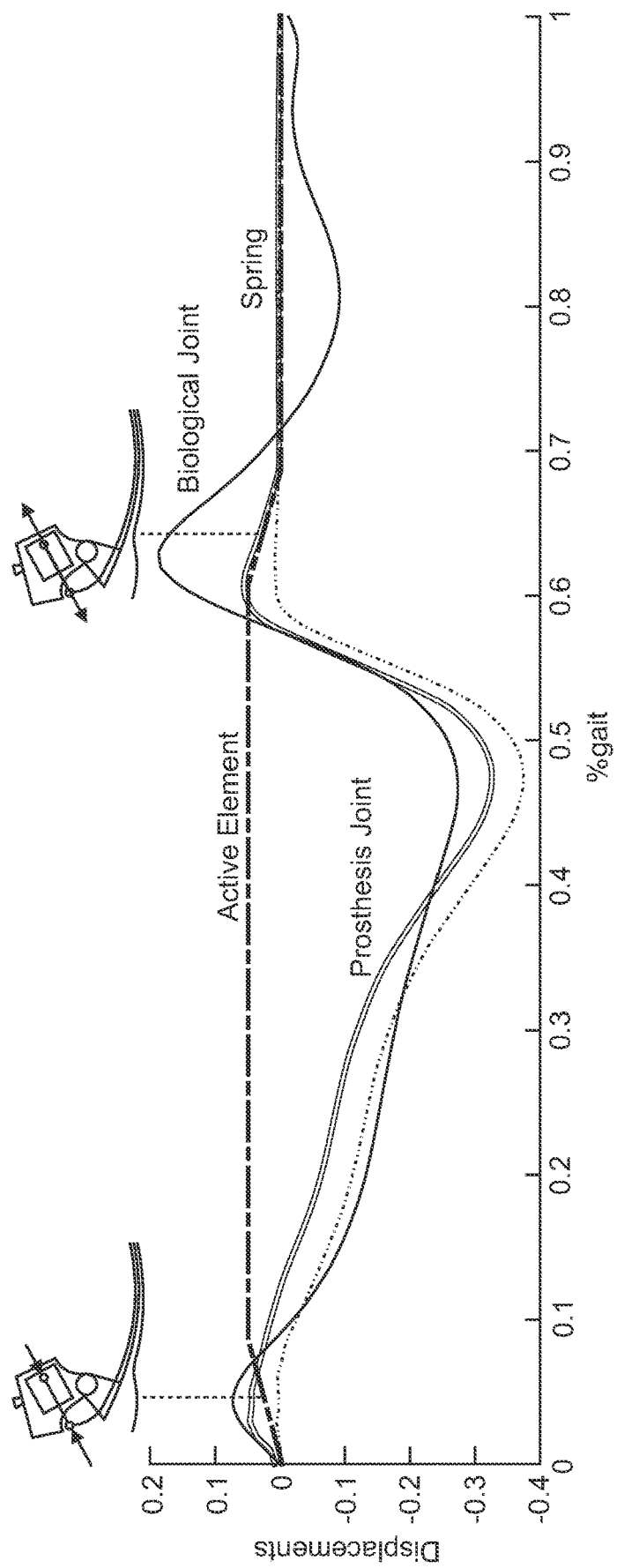
FIG. 13: Predicted prosthesis ankle joint, series spring, and active element displacements using the first control embodiment during level-ground walking.

In the first control embodiment, shown in FIG. 13, the prosthesis uses the amputees' body weight in conjunction with variable damping to vary the series J-spring 107 equilibrium position. FIG. 13 shows predicted prosthesis ankle joint, series spring, and active element displacements using the first control embodiment during level-ground walking. The active element position is set to a single position during stance using body weight and controlled damping. The swing equilibrium position is set to a fixed angle based on a return spring in the active element. Here the active element length is decreased to adjust the ankle spring equilibrium to a more plantarflexed position, whereas the active element length is increased to adjust the ankle spring equilibrium to a more dorsiflexed position. At heel strike, damping is reduced to allow the ankle to plantarflex to a desired angle due to active element length changes. Once the desired active element length and ankle angle is reached, damping is increased to lock the active element length, and consequently the ankle equilibrium position, for the remainder of the stance phase. At toe off, the damping is minimized to allow the equilibrium ankle position to return to zero (the neutral ankle angle when the base of the foot is generally perpendicular to the shank) before increasing again to the predicted early stance, foot strike value. This first control embodiment requires no active parallel motor to control the equilibrium position of the J-spring and will function with an active damper and passive parallel spring system. This embodiment would only use a small amount of electrical energy and still allow the prosthesis to adjust its spring equilibrium angle throughout gait. However, it is unable to adjust the equilibrium position during swing and would always produce net negative stance work during a walking gait cycle.

Figure 14:
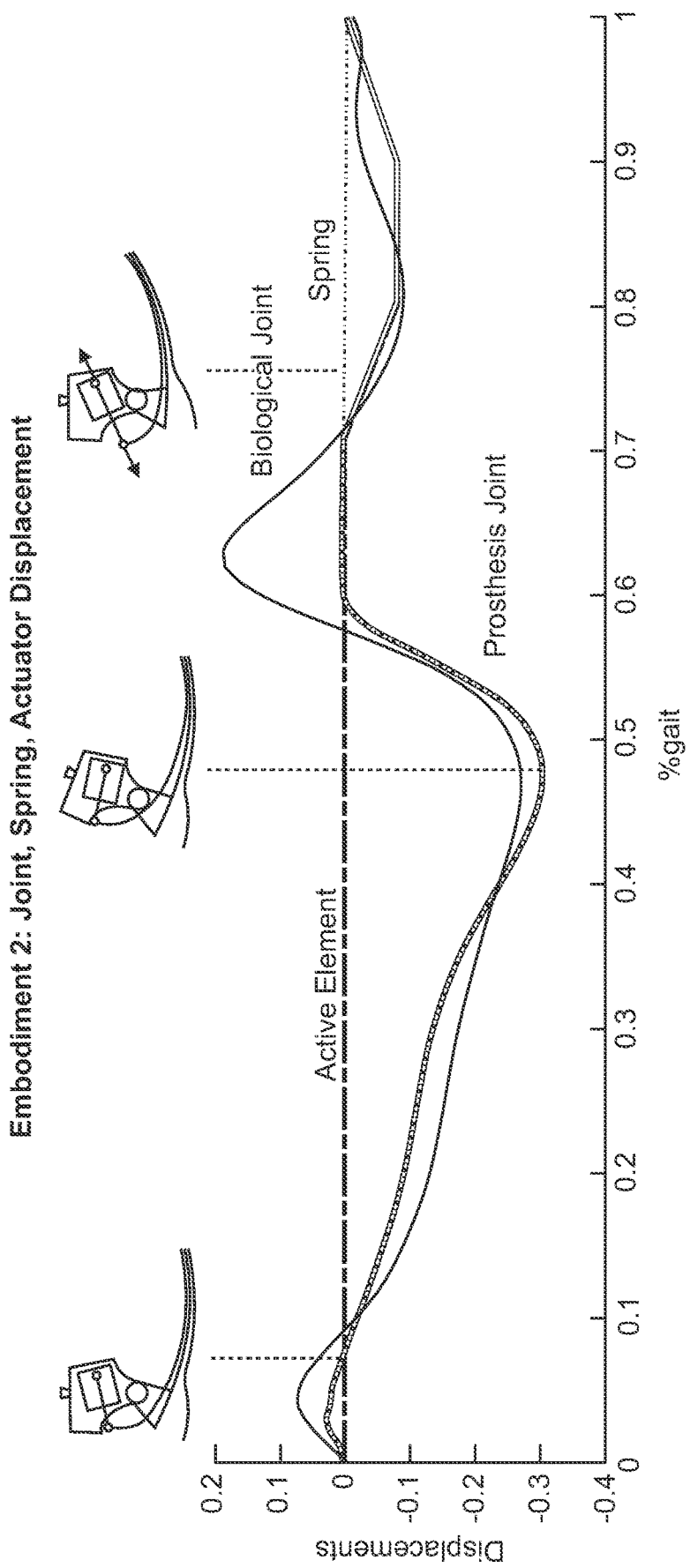
FIG. 14: Predicted prosthesis ankle joint, series spring, and active element displacements using the second control embodiment during level-ground walking.

In the second control embodiment, shown in FIG. 14, the prosthesis uses a small motor with a non-backdrivable screw to provide position control for the ankle joint when the prosthesis is unloaded during the swing phase, and passive energy storage and release while loaded during the stance phase. FIG. 14 shows predicted prosthesis ankle joint, series spring, and active element displacements using the second control embodiment during level-ground walking. The active element remains at a constant length during the entire stance phase with an active element length corresponding to a spring equilibrium ankle angle appropriate for the terrain slope. The toe is dorsiflexed and the spring equilibrium ankle angle is reset during swing. Here the active element length is decreased to adjust the ankle spring equilibrium to a more plantarflexed position, whereas the active element length is increased to adjust the ankle spring equilibrium to a more dorsiflexed position. When the computer-controlled prosthesis is off the ground during swing, it can move the linear actuator and cause the foot to plantar flex or dorsiflex depending on the requirements from the environment. Then when the foot is loaded at heel strike, the non-backdrivable transmission will maintain the equilibrium point for the large J-spring, which will then act like current commercially-available energy storage and return prosthetic ankles. As shown in FIG. 12, while walking, the prosthesis will provide passive energy storage when bodyweight is applied during early-stance and mid-stance, and return that elastic energy during late-stance. During swing, the actuator is able to set the angle of the ankle prior to heel strike based on information gathered by on- or offboard sensors connected to the computer system. This second embodiment would make use of a non-back-drivable transmission so that the size of the motor can be kept to a minimum. This embodiment would require a minor increase in energy over the first control embodiment and still allow the prosthesis to adjust its spring equilibrium angle to varying terrains, including slopes and stairs.

Figure 15:
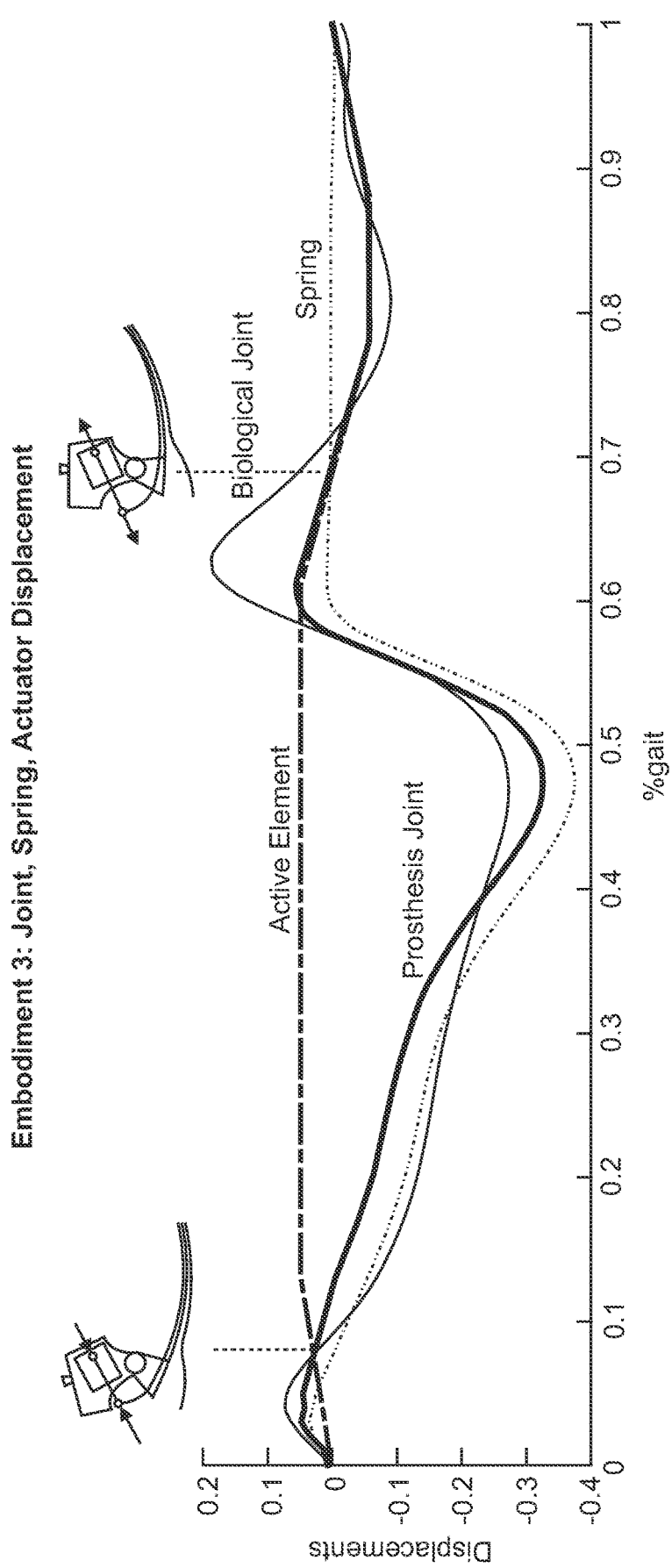
FIG. 15: Predicted joint, series spring, and active element displacements using the third control embodiment during level-ground walking.

The third control embodiment, shown in FIG. 15, uses a larger motor that is able to provide the same swing spring equilibrium control as the second embodiment, and allow for some adjustment under load during stance. FIG. 15 shows predicted joint, series spring, and active element displacements using the third control embodiment during level-ground walking. The active element lengthens at the start of stance to produce a slight plantarflexion which is held until toe off. The toe is dorsiflexed and the spring equilibrium ankle angle is reset during swing. Here the active element length is decreased to adjust the ankle spring equilibrium to a more plantarflexed position, whereas the active element length is increased to adjust the ankle spring equilibrium to a more dorsiflexed position. This added functionality is useful for the amputee when walking, standing on uneven terrain, or lowering themselves down stairs. Shown in FIG. 12, during Controlled Plantar Flexion from heel strike to the first forefoot contact, the third control embodiment lowers the toe by unwinding the screw through motor action, decreasing the active element length. This motor control action provides shock absorption and virtual damping while providing for a plantar flexed spring equilibrium ankle angle at the end of the Controlled Plantar Flexion gait phase. This new plantar flexed spring equilibrium angle is then maintained throughout Controlled Dorsiflexion and Push-off, enabling a toe-off ankle angle that is plantar flexed. The swing phase operation is then similar to the second control embodiment. The power requirements for the motor are still low, as the motor is working with the users' body weight to lower the toe, or plantar flex the ankle, during the Controlled Plantar Flexion phase of walking. This third control embodiment provides for an ankle-foot prosthesis that plantar flexes during terminal stance, as well as spring equilibrium control during the swing phase. However, the third control embodiment does not provide net positive mechanical work during the stance phase of walking.

Figure 16:
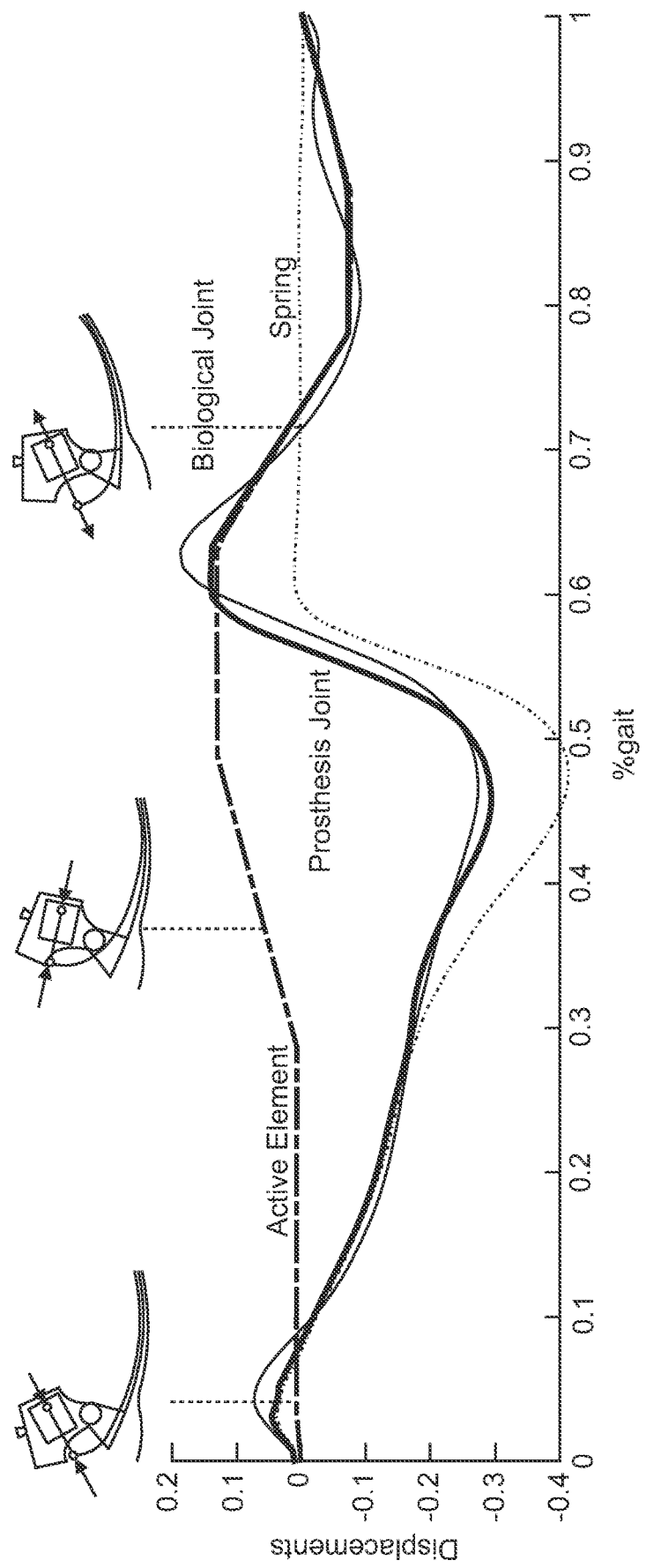
FIG. 16: Predicted joint, series spring, and active element displacements using the fourth control embodiment during level-ground walking.

The fourth control embodiment, shown in FIG. 16, uses a more powerful motor to allow the actuator to pull against the J-spring when the load on the prosthesis is high during Controlled Dorsiflexion. FIG. 16 shows predicted joint, series spring, and active element displacements using the fourth control embodiment during level-ground walking. The active element plantarflexes during heel strike to provide virtual damping and again during controlled dorsiflexion to stiffen spring and inject energy into the push-off. The toe is dorsiflexed and the spring equilibrium ankle angle is reset during swing. The results correspond to the detailed design in FIG. 8. Here the active element length is decreased to adjust the ankle spring equilibrium to a more plantarflexed position, whereas the active element length is increased to adjust the ankle spring equilibrium to a more dorsiflexed position. As shown in FIG. 12, this embodiment provides the same spring equilibrium control during both the swing and stance phases as the third control embodiment. However, the control embodiment also stores additional strain energy into the J-spring during Controlled Dorsiflexion phase of walking by actively doing mechanical work on the J-spring. This additional stored elastic energy within the large J-spring then allows for a more powerful push-off, or powered plantar flexion. This fourth control embodiment requires a larger motor than the three previous control embodiments and a semi-backdrivable or backdrivable transmission so as to provide positive net-work during the stance period which is important for comfortable level-ground walking, ramp ascent, and stair ascent. This embodiment also has an advantage over prior active devices in that it stores energy within the J-spring over the entire Controlled Dorsiflexion phase. This stored elastic energy is then released during push-off, lifting the body's center of mass upwards and forwards through elastic spring recoil. Such a rapid and powerful spring recoil provides the entirety of the mechanical power during push-off, without the active element continuing to do work on the series spring during this phase. Such a catapult control applied to the J-spring series elastic actuator provides for a smooth powered push-off with minimal acoustic noise. Once the ankle-foot prosthesis outputs high peak ankle power and net mechanical work during push-off, the ankle rapidly dorsiflexes upon entering the swing phase from a plantar flexed posture at the moment of toe-off. This strategy can also further reduce the energy requirements of the motor through a self-locking semi-backdrivable transmission once desired angles are reached (active element embodiment three) or locking the motor using an attached clutch (active element embodiment four).

Figure 17:
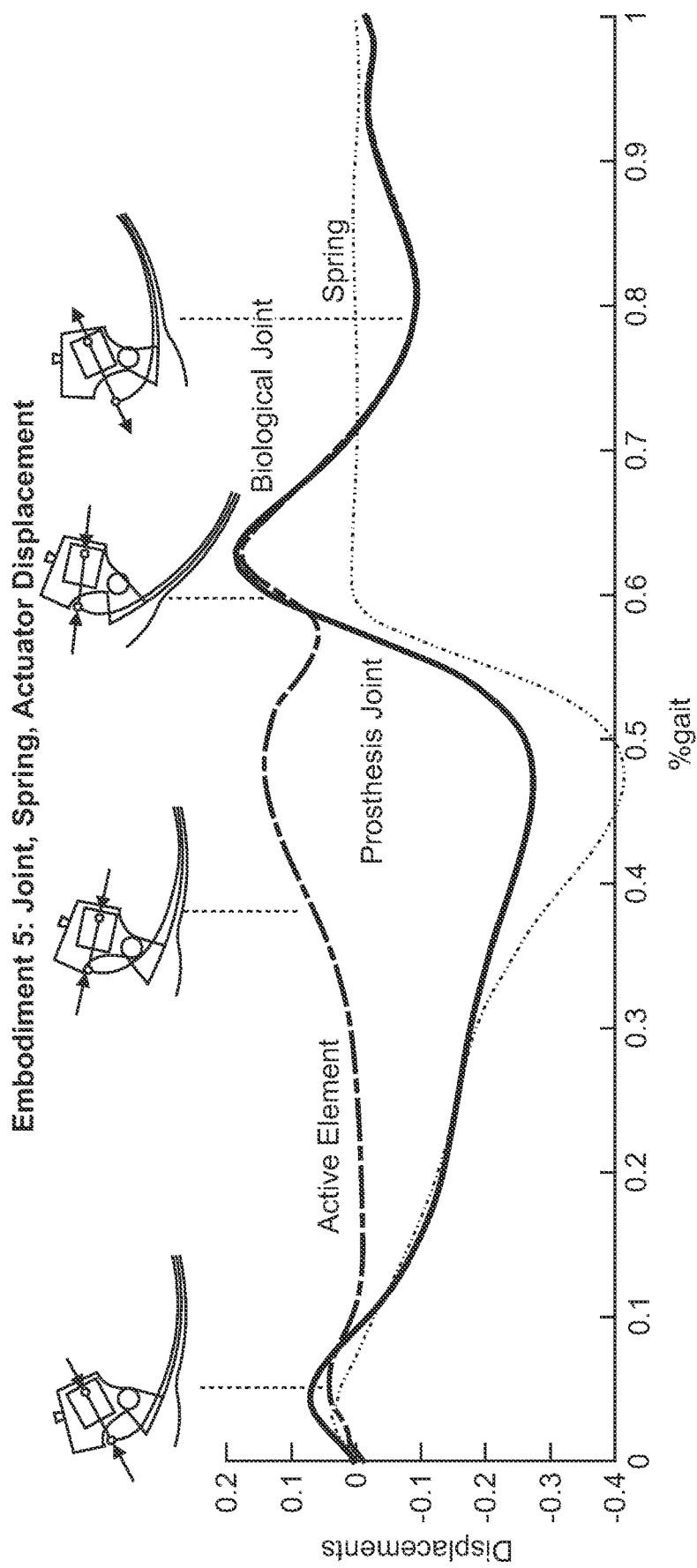
FIG. 17: Predicted joint, series spring, and active element displacements using the fifth control embodiment during level-ground walking.

The fifth control embodiment, shown in FIG. 17, uses a highly backdrivable transmission and a large motor to perform precise impedance and torque control throughout the gait cycle. FIG. 17 shows predicted joint, series spring, and active element displacements using the fifth control embodiment during level-ground walking. Active element displacement updates throughout gait to reproduce biological ankle angles. Here the active element length is decreased to adjust the ankle spring equilibrium to a more plantarflexed position, whereas the active element length is increased to adjust the ankle spring equilibrium to a more dorsiflexed position. For this control embodiment, the actuator could reproduce biological torque and angle trajectories through standard force control using onboard force sensors and/or joint encoders. FIG. 17 shows an example of a control system that repositions the active element throughout stance and swing to reproduce biological torques for the given spring stiffness. While the fifth control embodiment is the most capable of the controls presented here, it requires the most electrical power and has the greatest mechatronic design complexity.

The first active-element embodiment is capable of reproducing the first control embodiment. The second active-element embodiment is capable of both the first, second, and third control embodiments. In addition to the first, second, and third control embodiments, the third active-element embodiment is also capable of the fourth control embodiment. The fourth active-element embodiment is capable of all five control embodiments. It would be obvious to a person of ordinary skill in the art that the invention described herein could be used for any robotic ankle-foot device application, including prostheses, orthoses, exoskeletons or humanoid robotics.

While example embodiments have been particularly shown and described, it will be understood by those skilled in the art that various changes in form and details may be made therein without departing from the scope of the embodiments encompassed by the appended claims.

REFERENCES

U.S. Ser. No. 10/342,681B2—Artificial ankle-foot system with spring, variable-damping, and series-elastic actuator components U.S. Pat. No. 9,060,883B2—Biomimetic joint actuators
US20140088729A1—Powered Ankle-Foot Prosthesis The relevant teachings of all patents, published applications and references cited herein are incorporated by reference in their entirety.

What is claimed is:

1. An ankle-foot prosthesis comprising:
   a foot structure comprising an anterior portion and a foot keel leaf spring extending posteriorly from the anterior portion;
   an ankle-bearing block mounted to and above the foot keel leaf spring;
   a shank shell mounted to and above the ankle-bearing block at an ankle joint;
   a prosthetic shank interface mounted to the shank shell;
   an upper leaf spring extending posteriorly from the anterior portion of the foot structure above the keel leaf spring past the ankle-bearing block;
   a processor controlled active element extending along an active element axis between the shank shell and a posterior portion of the upper leaf spring and coupled to the shank shell at a shank shell rotational bearing and to the upper leaf spring at an upper leaf spring rotational bearing.

2. The ankle-foot prosthesis as claim in claim 1 further comprising a heel leaf spring extending posteriorly from the anterior portion below the foot keel leaf spring.

3. The ankle-foot prosthesis as claimed in claim 1 wherein the upper leaf spring curves upwardly from the anterior portion to the posterior portion of the upper leaf spring, the active element axis extending posteriorly from the shank shell rotational bearing to the upper leaf spring rotational bearing.

4. The ankle-foot prosthesis as claimed in claim 1 wherein, through a full operating range, the active element axis extends at or above a toe line extending from the upper leaf spring rotational bearing to an anterior end of the upper leaf spring.

5. The ankle-foot prosthesis as claimed in claim 1 wherein, at peak dorsiflexion, the active element axis extends about parallel to an anterior length of the upper leaf spring.

6. The ankle-foot prosthesis as claimed in claim 1 wherein, through a full operating range, the active element axis is within about 45° of being parallel to an anterior length of the upper leaf spring.

7. The ankle-foot prosthesis as claimed in claim 1 wherein the active element is a processor modulated damper with passive parallel return spring.

8. The ankle-foot prosthesis as claimed in claim 1 wherein the active element is a processor modulated damper operatively coupled to a motor configured to enable processor modulation of the active element length.

9. The ankle-foot prosthesis as claimed in claim 1 wherein the active element is a motor driven screw configured to enable processor modulation of the active element length.

10. The ankle-foot prosthesis as claimed in claim 9 wherein the screw is a roller screw.

11. The ankle-foot prosthesis as claimed in claim 9 wherein the screw is belt driven from the motor.

12. The ankle-foot prosthesis as claimed in claim 9 wherein the screw is direct driven from the motor.

13. The ankle-foot prosthesis as claimed in claim 9 further comprising a clutch or variable damper configured to lock the active element length.

14. The ankle-foot prosthesis as claimed in claim 1 further comprising the processor.

15. The ankle-foot prosthesis as claimed in claim 1 further comprising sensors that sense operation of the ankle-foot prosthesis and provide input to the processor for control of the active element.

16. The ankle-foot prosthesis as claimed in claim 1 further comprising at least one sensor from the group of sensors comprising inertia measurement units, joint encoders, motor encoders, force sensors, and distance sensors.

* * * * *